US012805961B2

(12) United States Patent
Ding et al.

(10) Patent No.: US 12,805,961 B2
(45) Date of Patent: Nov. 24, 2026

(54) ROBOTIC SURGICAL SYSTEM INCLUDING A COUPLER FOR CONNECTING A TOOL TO A MANIPULATOR AND METHODS OF USING THE COUPLER

(71) Applicant: MAKO Surgical Corp., Weston, FL (US)

(72) Inventors: Jienan Ding, Weston, FL (US); Thomas Trey Miller, Fort Lauderdale, FL (US); Amar Bhatt, Fort Lauderdale, FL (US); Matthew Guthart, Fort Lauderdale, FL (US); David Gene Bowling, Los Ranchos De Albuquerque, NM (US); Jeremiah Beers, Weston, FL (US); Robert Lee Boudreaux, Fort Lauderdale, FL (US)

(73) Assignee: MAKO Surgical Corp., Weston, FL (US)

( * ) Notice: Subject to any disclaimer, the term of this patent is extended or adjusted under 35 U.S.C. 154(b) by 1225 days.

(21) Appl. No.: 17/393,728

(22) Filed: Aug. 4, 2021

(65) Prior Publication Data

US 2022/0039898 A1 Feb. 10, 2022

Related U.S. Application Data

(60) Provisional application No. 63/061,266, filed on Aug. 5, 2020.

(51) Int. Cl.
*A61B 46/10* (2016.01)
*A61B 17/00* (2006.01)
(Continued)

(52) U.S. Cl.
CPC .............. *A61B 46/10* (2016.02); *A61B 34/30* (2016.02)

(58) Field of Classification Search
CPC ............................... A61B 46/10; A61B 34/30
See application file for complete search history.

(56) References Cited

U.S. PATENT DOCUMENTS

| | | | |
|---|---|---|---|
| 3,482,567 | A | 12/1969 | Donald |
| 3,483,494 | A | 12/1969 | Cromie |

(Continued)

FOREIGN PATENT DOCUMENTS

| | | | |
|---|---|---|---|
| AU | 754882 | B2 | 11/2002 |
| CN | 100464720 | C | 3/2009 |

(Continued)

OTHER PUBLICATIONS

Bateman, D.A., “Adjustable Mirror Mount Design Using Kinematic Principles” Dip. Tech.—Royal Aircraft Establishment—Technical Report No. 66349, Nov. 1966. U.D.C. No. 621.3-21: 531.1: 681.4. 28 pages.

(Continued)

*Primary Examiner* — Benjamin J Klein
*Assistant Examiner* — Thien Jason Tran
(74) *Attorney, Agent, or Firm* — Howard & Howard Attorneys PLLC

(57) ABSTRACT

A robotic surgical system includes a tool and a robotic manipulator including a plurality of links and a plurality of joints. The manipulator supports the tool for movement relative to a surgical site. A coupler interconnects the tool and the manipulator. The coupler includes a first coupling interface connectable to a distal link of the manipulator and a second coupling interface connectable to the tool. The coupler also includes a tracker to be detected by the localizer to determine a pose of the tool. The coupler is configured to cooperate with a drape to create a sterile field barrier between the tool and the robotic manipulator.

24 Claims, 19 Drawing Sheets

(51) Int. Cl.
*A61B 34/20* (2016.01)
*A61B 34/30* (2016.01)
*A61B 90/00* (2016.01)

(56) References Cited

U.S. PATENT DOCUMENTS 3,796,477 A 3/1974 Geraci
4,409,738 A 10/1983 Renander et al.
4,522,196 A 6/1985 Cunningham et al.
4,770,497 A 9/1988 Brown
5,042,981 A 8/1991 Gross
5,080,108 A 1/1992 Roth
5,086,401 A 2/1992 Glassman et al.
5,122,904 A 6/1992 Fujiwara et al.
5,184,601 A 2/1993 Putman
5,211,501 A 5/1993 Nakamura et al.
5,274,500 A 12/1993 Dunn
5,299,288 A 3/1994 Glassman et al.
5,408,409 A 4/1995 Glassman et al.
5,413,573 A 5/1995 Koivukangas
5,433,221 A 7/1995 Adair
5,441,042 A 8/1995 Putman
5,445,166 A 8/1995 Taylor
5,457,962 A 10/1995 Faries, Jr. et al.
5,467,223 A 11/1995 Cleveland, Jr. et al.
5,524,643 A 6/1996 Faries, Jr. et al.
5,574,561 A 11/1996 Boudreau et al.
5,591,119 A 1/1997 Adair
5,626,216 A 5/1997 Sperling et al.
5,642,956 A 7/1997 Hale
5,653,938 A 8/1997 Faries, Jr. et al.
5,669,152 A 9/1997 McMurtry
5,762,458 A 6/1998 Wang et al.
5,769,554 A 6/1998 Slocum
5,785,643 A 7/1998 Lynn
5,800,483 A 9/1998 Vought
5,816,252 A 10/1998 Faries, Jr. et al.
5,853,363 A 12/1998 Vought
5,855,583 A 1/1999 Wang et al.
5,857,467 A 1/1999 Faries, Jr. et al.
5,868,675 A 2/1999 Henrion et al.
5,876,328 A 3/1999 Fox et al.
5,891,020 A 4/1999 Luber et al.
5,960,794 A 10/1999 Shaw
6,013,087 A 1/2000 Adams et al.
6,050,981 A 4/2000 Lampropoulos et al.
6,063,095 A 5/2000 Wang et al.
6,065,898 A 5/2000 Hale
6,072,569 A 6/2000 Bowen
6,091,058 A 7/2000 Faries, Jr. et al.
6,102,044 A 8/2000 Naidyhorski
6,102,850 A 8/2000 Wang et al.
6,105,578 A 8/2000 Sommers et al.
6,116,966 A 9/2000 Little et al.
6,123,080 A 9/2000 Mohan et al.
6,132,368 A 10/2000 Cooper
6,167,296 A 12/2000 Shahidi
6,183,415 B1 2/2001 Gartner
6,228,089 B1 5/2001 Wahrburg
6,325,351 B1 12/2001 Hale et al.
6,330,837 B1 12/2001 Charles et al.
6,331,181 B1 12/2001 Tierney et al.
6,346,072 B1 2/2002 Cooper
6,357,445 B1 3/2002 Shaw
6,371,121 B1 4/2002 Faries, Jr. et al.
6,375,610 B2 4/2002 Verschuur
6,398,279 B1 6/2002 Kikut
6,416,462 B1 7/2002 Tovey et al.
6,431,530 B1 8/2002 Stamps et al.
6,434,416 B1 8/2002 Mizoguchi et al.
6,436,107 B1 8/2002 Wang et al.
6,460,436 B1 10/2002 Salzer et al.
6,460,677 B1 10/2002 Roscoe
6,471,172 B1 10/2002 Lemke et al.
6,491,612 B1 12/2002 Kurup et al.
6,491,701 B2 12/2002 Tierney et al.
6,533,455 B2 3/2003 Graumann et al.
6,533,594 B1 3/2003 Kurup
6,612,310 B2 9/2003 Sklar
6,661,955 B1 12/2003 Calvet et al.
6,676,669 B2 1/2004 Charles et al.
6,679,267 B2 1/2004 McNeirney et al.
6,692,141 B2 2/2004 Jesurun et al.
6,697,664 B2 2/2004 Kienzle, III et al.
6,699,177 B1 3/2004 Wang et al.
6,720,988 B1 4/2004 Gere et al.
6,729,589 B2 5/2004 Shelef
6,746,172 B2 6/2004 Culpepper
6,755,195 B1 6/2004 Lemke et al.
6,757,582 B2 6/2004 Brisson et al.
6,804,547 B2 10/2004 Pelzer et al.
6,805,453 B2 10/2004 Spetzler et al.
6,810,881 B2 11/2004 Faries, Jr. et al.
6,840,895 B2 1/2005 Perry et al.
6,843,252 B2 1/2005 Harrison et al.
6,860,271 B2 3/2005 Faries, Jr. et al.
6,863,071 B2 3/2005 Annett et al.
6,866,671 B2 3/2005 Tierney et al.
6,910,485 B2 6/2005 Faries, Jr. et al.
6,918,395 B2 7/2005 Faries, Jr. et al.
6,945,814 B2 9/2005 Snape et al.
7,002,102 B2 2/2006 Münch et al.
7,008,373 B2 3/2006 Stoianovici et al.
7,027,893 B2 4/2006 Perry et al.
7,043,961 B2 5/2006 Pandey et al.
7,044,132 B2 5/2006 Masini
7,048,745 B2 5/2006 Tierney et al.
7,074,180 B2 7/2006 Bertolero et al.
7,076,286 B2 7/2006 Mizoguchi et al.
7,118,582 B1 10/2006 Wang et al.
7,122,032 B2 10/2006 Shinmura et al.
7,137,763 B2 11/2006 Lawson
7,166,114 B2 1/2007 Moctezuma De La Barrera et al.
7,173,779 B2 2/2007 Shelef
7,252,453 B1 8/2007 Little
7,328,086 B2 2/2008 Perry et al.
7,331,967 B2 2/2008 Lee et al.
7,347,210 B2 3/2008 Faries, Jr. et al.
7,350,373 B1 4/2008 Faries, Jr. et al.
7,357,774 B2 4/2008 Cooper
7,418,966 B2 9/2008 Faries, Jr. et al.
7,422,107 B2 9/2008 Bums et al.
7,524,320 B2 4/2009 Tierney et al.
7,559,265 B2 7/2009 Mizuno
7,666,191 B2 2/2010 Orban, III et al.
7,699,855 B2 4/2010 Anderson et al.
7,726,564 B2 6/2010 Goldbach
7,727,244 B2 6/2010 Orban, III et al.
7,775,213 B2 8/2010 Henke-Sarmento et al.
7,779,716 B2 8/2010 Dellach et al.
7,789,874 B2 9/2010 Yu et al.
7,819,885 B2 10/2010 Cooper
7,820,446 B2 10/2010 Feilkas et al.
7,850,602 B2 12/2010 Humble et al.
7,850,642 B2 12/2010 Moll et al.
7,886,743 B2 2/2011 Cooper et al.
7,947,050 B2 5/2011 Lee et al.
7,947,051 B2 5/2011 Lee et al.
7,955,322 B2 6/2011 Devengenzo et al.
7,959,860 B2 6/2011 Faries, Jr. et al.
7,963,288 B2 6/2011 Rosenberg et al.
7,963,913 B2 6/2011 Devengenzo et al.
7,972,298 B2 7/2011 Wallace et al.
7,974,681 B2 7/2011 Wallace et al.
8,005,537 B2 8/2011 Hlavka et al.
8,005,570 B2 8/2011 Gloden et al.
8,010,180 B2 8/2011 Quaid et al.
8,021,326 B2 9/2011 Moll et al.
8,052,636 B2 11/2011 Moll et al.
8,054,184 B2 11/2011 Cline et al.
8,074,657 B2 12/2011 Scott et al.
8,082,064 B2 12/2011 Kay
8,100,133 B2 1/2012 Mintz et al.
8,105,319 B2 1/2012 Doyle et al.

(56) References Cited

U.S. PATENT DOCUMENTS 8,105,338 B2 1/2012 Anderson et al.
8,108,072 B2 1/2012 Zhao et al.
8,132,816 B2 3/2012 Norton et al.
8,142,447 B2 3/2012 Cooper et al.
8,146,825 B1 4/2012 Prpa
8,148,666 B2 4/2012 Faries, Jr. et al.
8,182,469 B2 5/2012 Anderson et al.
8,182,470 B2 5/2012 Devengenzo et al.
8,190,238 B2 5/2012 Moll et al.
8,196,586 B2 6/2012 Henke-Sarmento et al.
8,202,278 B2 6/2012 Orban, III et al.
8,206,053 B2 6/2012 Bennett et al.
8,206,406 B2 6/2012 Orban, III
8,209,840 B2 7/2012 Norton
8,216,250 B2 7/2012 Orban, III et al.
8,219,177 B2 7/2012 Smith et al.
8,219,178 B2 7/2012 Smith et al.
8,220,468 B2 7/2012 Cooper et al.
8,225,495 B2 7/2012 Dehler
8,241,208 B2 8/2012 Jiang et al.
8,257,303 B2 9/2012 Moll et al.
8,264,767 B2 9/2012 Nozawa
8,273,076 B2 9/2012 Devengenzo et al.
8,277,505 B1 10/2012 Doty
8,286,637 B2 10/2012 Kaska
8,311,626 B2 11/2012 Hlavka et al.
8,333,755 B2 12/2012 Cooper et al.
8,375,808 B2 2/2013 Blumenkranz et al.
8,394,054 B2 3/2013 Wallace et al.
8,409,136 B2 4/2013 Wallace et al.
8,413,948 B2 4/2013 Kemeny
8,460,277 B2 6/2013 Suarez et al.
8,464,722 B2 6/2013 Chua
8,469,947 B2 6/2013 Devengenzo et al.
8,500,132 B2 8/2013 Norton
8,529,582 B2 9/2013 Devengenzo et al.
8,533,930 B2 9/2013 Norton
8,534,848 B2 9/2013 Hauri et al.
8,548,779 B2 10/2013 Ortmaier et al.
8,601,667 B2 12/2013 Norton
8,602,031 B2 12/2013 Reis et al.
8,608,773 B2 12/2013 Tierney et al.
8,640,706 B2 2/2014 Skora et al.
8,662,082 B2 3/2014 Bogojevic et al.
8,672,922 B2 3/2014 Loh et al.
8,678,009 B2 3/2014 Hagn
8,720,448 B2 5/2014 Reis et al.
8,740,881 B2 6/2014 Ortmaier et al.
8,746,252 B2 6/2014 McGrogan et al.
8,747,288 B2 6/2014 Strotzer et al.
8,776,800 B2 7/2014 Skora et al.
8,784,435 B2 7/2014 Cooper et al.
8,794,993 B2 8/2014 Norton
8,800,939 B2 8/2014 Karsak et al.
8,844,538 B2 9/2014 Stang
8,857,821 B2 10/2014 Norton et al.
8,888,764 B2 11/2014 Devengenzo et al.
8,894,634 B2 11/2014 Devengenzo et al.
8,910,637 B2 12/2014 Winer
8,945,095 B2 2/2015 Blumenkranz et al.
8,971,597 B2 3/2015 Zhao et al.
8,992,113 B2 3/2015 Campagna et al.
8,998,799 B2 4/2015 Orban, III et al.
8,998,930 B2 4/2015 Orban, III
9,008,757 B2 4/2015 Wu
9,033,958 B2 5/2015 Mailloux et al.
9,044,269 B2 6/2015 Noerlein
9,078,685 B2 7/2015 Smith et al.
9,096,033 B2 8/2015 Holop et al.
RE45,681 E 9/2015 Perry et al.
9,119,655 B2 9/2015 Bowling et al.
9,161,816 B2 10/2015 Ball et al.
9,168,103 B2 10/2015 Hladio et al.
9,194,531 B2 11/2015 Shelef et al.
9,204,933 B2 12/2015 Reis et al.
9,241,771 B2 1/2016 Kostrzewski et al.
9,254,572 B2 2/2016 Strotzer
9,259,276 B2 2/2016 Mintz et al.
9,259,277 B2 2/2016 Rogers et al.
9,265,582 B2 2/2016 Riviere et al.
9,271,804 B2 3/2016 Wu
9,283,041 B2 3/2016 Adams
9,283,048 B2 3/2016 Kostrzewski et al.
9,295,521 B2 3/2016 Pack et al.
9,307,945 B2 4/2016 Campista
9,320,568 B2 4/2016 Orban, III et al.
9,339,342 B2 5/2016 Prisco et al.
9,339,346 B2 5/2016 Malackowski
9,439,732 B2 9/2016 Devengenzo et al.
9,452,020 B2 9/2016 Griffiths et al.
9,539,060 B2 1/2017 Lightcap et al.
9,566,122 B2 2/2017 Bowling et al.
9,629,680 B2 4/2017 Winer
9,668,768 B2 6/2017 Piron et al.
9,687,312 B2 6/2017 Dachs, II et al.
9,713,498 B2 7/2017 Malackowski et al.
9,713,509 B2 7/2017 Schuh et al.
9,714,737 B2 7/2017 Nishikawa
9,724,163 B2 8/2017 Orban
9,724,830 B2 8/2017 Norton et al.
9,731,392 B2 8/2017 Takla et al.
9,737,373 B2 8/2017 Schuh
9,750,510 B2 9/2017 Kostrzewski et al.
9,833,292 B2 12/2017 Kostrzewski et al.
9,883,915 B2 2/2018 Rogers et al.
9,895,813 B2 2/2018 Blumenkranz et al.
9,981,391 B2 5/2018 Kalb et al.
9,993,310 B2 6/2018 Pecora
9,993,313 B2 6/2018 Schuh et al.
10,004,562 B2 6/2018 Kostrzewski et al.
10,005,184 B2 6/2018 Gerio et al.
10,016,244 B2 7/2018 Cooper et al.
10,022,193 B2 7/2018 Cooper et al.
10,034,716 B2 7/2018 Crawford et al.
10,039,605 B2 8/2018 Kostrzewski et al.
10,039,610 B2 8/2018 Allen
10,045,828 B2 8/2018 Dachs, II et al.
10,046,465 B2 8/2018 Goto et al.
10,047,908 B1 8/2018 Bohle et al.
10,052,761 B2 8/2018 Langenfeld
10,058,394 B2 8/2018 Johnson et al.
10,076,844 B2 9/2018 Rizk
10,085,803 B2 10/2018 Higuchi et al.
10,105,855 B2 10/2018 Kalb et al.
10,136,954 B2 11/2018 Johnson et al.
10,149,731 B2 12/2018 Adams
10,151,423 B2 12/2018 Shelef et al.
10,172,678 B2 1/2019 Smith et al.
10,188,475 B2 1/2019 Chua et al.
10,206,749 B2 2/2019 Cleary et al.
10,213,267 B2 2/2019 King et al.
10,226,219 B2 3/2019 Cheatham, III et al.
10,231,791 B2 3/2019 Leboeuf, II et al.
10,235,737 B2 3/2019 Cheatham, III et al.
10,258,416 B2 4/2019 Mintz et al.
10,265,869 B2 4/2019 Lohmeier et al.
10,271,911 B2 4/2019 Cooper et al.
10,278,659 B2 5/2019 Kim
10,285,767 B2 5/2019 Marinchak
10,293,497 B2 5/2019 Lohmeier et al.
10,327,849 B2 6/2019 Post
10,335,242 B2 7/2019 Devengenzo et al.
10,342,625 B2 7/2019 Loh et al.
10,342,636 B2 7/2019 Nowatschin et al.
10,357,324 B2 7/2019 Flatt et al.
10,384,356 B2 8/2019 Lohmeier et al.
10,398,522 B2 9/2019 Czajka, Jr. et al.
10,405,929 B1 9/2019 Seltmann et al.
10,433,925 B2 10/2019 Shelton, IV et al.
10,485,619 B2 11/2019 Rogers et al.
10,485,621 B2 11/2019 Morrissette et al.
10,537,358 B2 1/2020 McGrogan et al.
10,537,400 B2 1/2020 Dachs, II et al.
10,543,051 B2 1/2020 Schena et al.

(56) References Cited

U.S. PATENT DOCUMENTS

| | | | |
|---|---|---|---|
| 10,548,673 | B2 | 2/2020 | Harris et al. |
| 10,582,980 | B2 | 3/2020 | Scheib et al. |
| 10,603,126 | B2 | 3/2020 | Karguth et al. |
| 10,610,312 | B2 | 4/2020 | Srivastava et al. |
| 10,624,710 | B2 | 4/2020 | Crawford et al. |
| 10,639,110 | B2 | 5/2020 | Hares |
| 10,660,715 | B2 | 5/2020 | Dozeman |
| 10,772,692 | B1 | 9/2020 | Li et al. |
| 10,792,107 | B2 | 10/2020 | Hoffman et al. |
| 10,952,796 | B2 | 3/2021 | Arata et al. |
| 11,033,343 | B2 | 6/2021 | Dozeman |
| 11,096,754 | B2 | 8/2021 | Soto et al. |
| 11,129,681 | B2 | 9/2021 | Amiot et al. |
| 11,172,994 | B1 | 11/2021 | Seltmann et al. |
| 11,278,360 | B2 | 3/2022 | Cascarano et al. |
| 2002/0082498 | A1 | 6/2002 | Wendt et al. |
| 2002/0137358 | A1 | 9/2002 | Binnard et al. |
| 2003/0083673 | A1 | 5/2003 | Tierney et al. |
| 2004/0077939 | A1 | 4/2004 | Graumann |
| 2004/0106894 | A1 | 6/2004 | Hunter et al. |
| 2004/0143243 | A1 | 7/2004 | Wahrburg |
| 2005/0088763 | A1 | 4/2005 | Weaver et al. |
| 2005/0124988 | A1 | 6/2005 | Terrill-Grisoni et al. |
| 2006/0016061 | A1 | 1/2006 | Shelef |
| 2006/0100610 | A1 | 5/2006 | Wallace et al. |
| 2006/0161138 | A1 | 7/2006 | Orban, III et al. |
| 2006/0191540 | A1 | 8/2006 | Lamprich et al. |
| 2006/0225529 | A1 | 10/2006 | Fischer et al. |
| 2006/0232837 | A1 | 10/2006 | Shelef |
| 2006/0264921 | A1 | 11/2006 | Deutsch et al. |
| 2007/0055291 | A1 | 3/2007 | Birkmeyer et al. |
| 2007/0231063 | A1 | 10/2007 | Tsutsumi et al. |
| 2007/0267028 | A1 | 11/2007 | Junk |
| 2007/0282311 | A1 | 12/2007 | Scott et al. |
| 2008/0119339 | A1 | 5/2008 | Oliver |
| 2008/0147089 | A1 | 6/2008 | Loh et al. |
| 2008/0182738 | A1 | 7/2008 | Grunke et al. |
| 2008/0218770 | A1 | 9/2008 | Moll et al. |
| 2008/0236598 | A1 | 10/2008 | Gobel |
| 2008/0281301 | A1 | 11/2008 | DeBoer et al. |
| 2009/0088772 | A1 | 4/2009 | Blumenkranz |
| 2009/0248039 | A1 | 10/2009 | Cooper et al. |
| 2009/0306499 | A1 | 12/2009 | Van Vorhis et al. |
| 2010/0009825 | A1 | 1/2010 | Norton et al. |
| 2010/0065068 | A1 | 3/2010 | Hamazaki et al. |
| 2010/0166496 | A1 | 7/2010 | Bennett et al. |
| 2010/0170519 | A1 | 7/2010 | Romo et al. |
| 2010/0241137 | A1 | 9/2010 | Doyle et al. |
| 2010/0268249 | A1 | 10/2010 | Stuart |
| 2010/0268250 | A1 | 10/2010 | Stuart et al. |
| 2010/0308195 | A1 | 12/2010 | Yu et al. |
| 2011/0015650 | A1 | 1/2011 | Choi et al. |
| 2011/0087238 | A1 | 4/2011 | Wang et al. |
| 2011/0088702 | A1 | 4/2011 | King et al. |
| 2011/0125022 | A1 | 5/2011 | Lazebnik |
| 2011/0154645 | A1 | 6/2011 | Morgan |
| 2011/0190790 | A1 | 8/2011 | Summerer et al. |
| 2011/0213383 | A1 | 9/2011 | Lee et al. |
| 2011/0238083 | A1 | 9/2011 | Moll et al. |
| 2011/0277775 | A1 | 11/2011 | Holop et al. |
| 2011/0277776 | A1 | 11/2011 | McGrogan et al. |
| 2012/0065472 | A1 | 3/2012 | Doyle et al. |
| 2012/0071752 | A1 | 3/2012 | Sewell et al. |
| 2012/0071821 | A1 | 3/2012 | Yu |
| 2012/0071822 | A1 | 3/2012 | Romo et al. |
| 2012/0071894 | A1 | 3/2012 | Tanner et al. |
| 2012/0071895 | A1 | 3/2012 | Stahler et al. |
| 2012/0080040 | A1 | 4/2012 | Skora et al. |
| 2012/0080041 | A1 | 4/2012 | Skora et al. |
| 2012/0083799 | A1 | 4/2012 | Chen et al. |
| 2012/0083825 | A1 | 4/2012 | Stroup et al. |
| 2012/0191107 | A1 | 7/2012 | Tanner et al. |
| 2012/0209174 | A1 | 8/2012 | Moll et al. |
| 2012/0209291 | A1 | 8/2012 | Anderson et al. |
| 2012/0232566 | A1 | 9/2012 | Orban, III et al. |
| 2012/0239060 | A1 | 9/2012 | Orban, III |
| 2012/0247489 | A1 | 10/2012 | Orban, III et al. |
| 2012/0289974 | A1 | 11/2012 | Rogers et al. |
| 2012/0301067 | A1 | 11/2012 | Morgan |
| 2012/0305650 | A1 | 12/2012 | Prpa |
| 2012/0312308 | A1 | 12/2012 | Allen |
| 2013/0035537 | A1 | 2/2013 | Wallace et al. |
| 2013/0092177 | A1 | 4/2013 | Chua et al. |
| 2013/0174858 | A1 | 7/2013 | Annett |
| 2013/0211401 | A1 | 8/2013 | Bailey et al. |
| 2013/0231679 | A1 | 9/2013 | Wallace et al. |
| 2013/0247921 | A1 | 9/2013 | Dye et al. |
| 2013/0317519 | A1 | 11/2013 | Romo et al. |
| 2013/0325048 | A1 | 12/2013 | Weiman |
| 2013/0331858 | A1 | 12/2013 | Devengenzo et al. |
| 2014/0039681 | A1 | 2/2014 | Bowling et al. |
| 2014/0128885 | A1 | 5/2014 | Dachs, II et al. |
| 2014/0130810 | A1 | 5/2014 | Azizian et al. |
| 2014/0171965 | A1 | 6/2014 | Loh et al. |
| 2014/0261456 | A1 | 9/2014 | Malackowski et al. |
| 2014/0275955 | A1 | 9/2014 | Crawford et al. |
| 2014/0276949 | A1 | 9/2014 | Staunton et al. |
| 2014/0318551 | A1 | 10/2014 | Daly |
| 2014/0326254 | A1 | 11/2014 | McGrogan et al. |
| 2015/0003789 | A1 | 1/2015 | Webler et al. |
| 2015/0045813 | A1 | 2/2015 | Kostrzewski et al. |
| 2015/0047647 | A1 | 2/2015 | Winer |
| 2015/0073437 | A1 | 3/2015 | Devengenzo et al. |
| 2015/0100066 | A1 | 4/2015 | Kostrzewski et al. |
| 2015/0133960 | A1 | 5/2015 | Lohmeier et al. |
| 2015/0142012 | A1 | 5/2015 | Lohmeier et al. |
| 2015/0148817 | A1 | 5/2015 | Lohmeier et al. |
| 2015/0148818 | A1 | 5/2015 | Lohmeier et al. |
| 2015/0150638 | A1 | 6/2015 | Lohmeier et al. |
| 2015/0173841 | A1 | 6/2015 | Orban |
| 2015/0196365 | A1 | 7/2015 | Kostrzewski et al. |
| 2015/0202009 | A1 | 7/2015 | Nussbaumer et al. |
| 2015/0223897 | A1 | 8/2015 | Kostrzewski et al. |
| 2015/0305815 | A1 | 10/2015 | Holop et al. |
| 2015/0335390 | A1 | 11/2015 | Gill |
| 2015/0342685 | A1 | 12/2015 | Livesey |
| 2015/0366624 | A1 | 12/2015 | Kostrzewski et al. |
| 2016/0008011 | A1 | 1/2016 | Kostrzewski |
| 2016/0008073 | A1 | 1/2016 | Pecora |
| 2016/0039059 | A1 | 2/2016 | Takla et al. |
| 2016/0052146 | A1 | 2/2016 | Berrocal et al. |
| 2016/0058513 | A1 | 3/2016 | Giorgi et al. |
| 2016/0059424 | A1 | 3/2016 | Zachary et al. |
| 2016/0081753 | A1 | 3/2016 | Kostrzewski |
| 2016/0081754 | A1 | 3/2016 | Kostrzewski et al. |
| 2016/0128789 | A1 | 5/2016 | Kostrzewski et al. |
| 2016/0151120 | A1 | 6/2016 | Kostrzewski et al. |
| 2016/0184036 | A1 | 6/2016 | Solomon et al. |
| 2016/0184037 | A1 | 6/2016 | Cooper et al. |
| 2016/0220320 | A1 | 8/2016 | Crawford et al. |
| 2016/0235492 | A1 | 8/2016 | Morard et al. |
| 2016/0242858 | A1 | 8/2016 | Moctezuma de la Barrera et al. |
| 2016/0242861 | A1 | 8/2016 | Flatt et al. |
| 2016/0256225 | A1 | 9/2016 | Crawford et al. |
| 2016/0302871 | A1 | 10/2016 | Gregerson et al. |
| 2016/0310224 | A1 | 10/2016 | Dye et al. |
| 2016/0324583 | A1 | 11/2016 | Kheradpir et al. |
| 2016/0338783 | A1 | 11/2016 | Romo et al. |
| 2016/0361124 | A1 | 12/2016 | Dachs, II et al. |
| 2016/0361131 | A1 | 12/2016 | Dachs, II et al. |
| 2016/0374766 | A1 | 12/2016 | Schuh |
| 2017/0000572 | A1 | 1/2017 | Moctezuma de la Barrera et al. |
| 2017/0007334 | A1 | 1/2017 | Crawford et al. |
| 2017/0020630 | A1 | 1/2017 | Johnson et al. |
| 2017/0056116 | A1 | 3/2017 | Kostrzewski, Phd |
| 2017/0065357 | A1 | 3/2017 | Schuh |
| 2017/0071685 | A1 | 3/2017 | Crawford et al. |
| 2017/0071691 | A1 | 3/2017 | Crawford et al. |
| 2017/0079727 | A1 | 3/2017 | Crawford et al. |
| 2017/0086934 | A1 | 3/2017 | Devengenzo et al. |
| 2017/0119339 | A1 | 5/2017 | Johnson et al. |
| 2017/0144230 | A1 | 5/2017 | Rosso et al. |
| 2017/0165012 | A1 | 6/2017 | Chaplin et al. |
| 2017/0172669 | A1 | 6/2017 | Berkowitz et al. |

(56) References Cited

U.S. PATENT DOCUMENTS

| | | | |
|---|---|---|---|
| 2017/0172671 | A1 | 6/2017 | Miller et al. |
| 2017/0172674 | A1 | 6/2017 | Hanuschik et al. |
| 2017/0181801 | A1 | 6/2017 | Griffiths et al. |
| 2017/0239003 | A1 | 8/2017 | Crawford et al. |
| 2017/0239006 | A1 | 8/2017 | Crawford et al. |
| 2017/0239007 | A1 | 8/2017 | Crawford et al. |
| 2017/0245944 | A1 | 8/2017 | Crawford et al. |
| 2017/0245946 | A1 | 8/2017 | Tabandeh et al. |
| 2017/0245951 | A1 | 8/2017 | Crawford et al. |
| 2017/0252114 | A1 | 9/2017 | Crawford et al. |
| 2017/0258533 | A1 | 9/2017 | Crawford et al. |
| 2017/0258535 | A1 | 9/2017 | Crawford et al. |
| 2017/0265774 | A1 | 9/2017 | Johnson et al. |
| 2017/0281145 | A1 | 10/2017 | Crawford et al. |
| 2017/0290632 | A1 | 10/2017 | Nakatsu et al. |
| 2017/0304013 | A1 | 10/2017 | Crawford et al. |
| 2017/0312039 | A1 | 11/2017 | Crawford et al. |
| 2017/0333057 | A1 | 11/2017 | Kostrzewski et al. |
| 2017/0333136 | A1 | 11/2017 | Hladio et al. |
| 2017/0333147 | A1 | 11/2017 | Bemstein |
| 2017/0348061 | A1 | 12/2017 | Joshi et al. |
| 2017/0348063 | A1 | 12/2017 | Braun et al. |
| 2017/0354468 | A1 | 12/2017 | Johnson et al. |
| 2017/0360517 | A1 | 12/2017 | Crawford et al. |
| 2017/0360521 | A1 | 12/2017 | Johnson |
| 2017/0367782 | A1 | 12/2017 | Schuh et al. |
| 2018/0000047 | A1 | 1/2018 | Stone |
| 2018/0000472 | A1 | 1/2018 | Beira |
| 2018/0008353 | A1 | 1/2018 | Kostrzewski et al. |
| 2018/0008358 | A1 | 1/2018 | Kostrzewski et al. |
| 2018/0014888 | A1 | 1/2018 | Bonny et al. |
| 2018/0021096 | A1 | 1/2018 | Kostrzewski et al. |
| 2018/0036091 | A1 | 2/2018 | Scholan |
| 2018/0042684 | A1 | 2/2018 | Kostrzewski et al. |
| 2018/0055593 | A1 | 3/2018 | Schlatterer |
| 2018/0064497 | A1 | 3/2018 | Hussain et al. |
| 2018/0071029 | A1 | 3/2018 | Srimohanarajah et al. |
| 2018/0110572 | A1 | 4/2018 | Flatt |
| 2018/0110573 | A1 | 4/2018 | Kostrzewski |
| 2018/0110576 | A1 | 4/2018 | Kopp |
| 2018/0116746 | A1 | 5/2018 | Lennertz et al. |
| 2018/0125597 | A1 | 5/2018 | Gogarty et al. |
| 2018/0126546 | A1 | 5/2018 | Vaders |
| 2018/0132839 | A1 | 5/2018 | Friedrich et al. |
| 2018/0132959 | A1 | 5/2018 | Marshall et al. |
| 2018/0140371 | A1 | 5/2018 | Hares et al. |
| 2018/0147018 | A1 | 5/2018 | Crawford et al. |
| 2018/0168749 | A1 | 6/2018 | Dozeman |
| 2018/0168750 | A1 | 6/2018 | Staunton et al. |
| 2018/0168752 | A1 | 6/2018 | Scheib et al. |
| 2018/0168753 | A1 | 6/2018 | Scheib et al. |
| 2018/0168761 | A1 | 6/2018 | Vargas et al. |
| 2018/0168762 | A1 | 6/2018 | Scheib et al. |
| 2018/0168763 | A1 | 6/2018 | Scheib et al. |
| 2018/0199951 | A1 | 7/2018 | Chappuis et al. |
| 2018/0199999 | A1 | 7/2018 | Syverson et al. |
| 2018/0200002 | A1 | 7/2018 | Kostrzewski et al. |
| 2018/0200014 | A1 | 7/2018 | Bonny et al. |
| 2018/0206931 | A1 | 7/2018 | Scheib |
| 2018/0214221 | A1 | 8/2018 | Crawford et al. |
| 2018/0215051 | A1 | 8/2018 | Kan |
| 2018/0221098 | A1 | 8/2018 | Forsyth et al. |
| 2018/0256259 | A1 | 9/2018 | Crawford |
| 2018/0263714 | A1 | 9/2018 | Kostrzewski et al. |
| 2018/0271604 | A1 | 9/2018 | Grout et al. |
| 2018/0271616 | A1 | 9/2018 | Schuh et al. |
| 2018/0279993 | A1 | 10/2018 | Crawford et al. |
| 2018/0280097 | A1 | 10/2018 | Cooper et al. |
| 2018/0289431 | A1 | 10/2018 | Draper et al. |
| 2018/0289432 | A1 | 10/2018 | Kostrzewski et al. |
| 2018/0289438 | A1 | 10/2018 | Pennoyer |
| 2018/0296283 | A1 | 10/2018 | Crawford et al. |
| 2018/0296292 | A1 | 10/2018 | Yamasaki et al. |
| 2018/0304475 | A1 | 10/2018 | Zachary et al. |
| 2018/0310808 | A1 | 11/2018 | Laser et al. |
| 2018/0310997 | A1 | 11/2018 | Peine et al. |
| 2018/0311001 | A1 | 11/2018 | Prisco |
| 2018/0316139 | A1 | 11/2018 | Berrocal et al. |
| 2018/0325609 | A1 | 11/2018 | Kostrzewski et al. |
| 2018/0325610 | A1 | 11/2018 | Cameron et al. |
| 2018/0325616 | A1 | 11/2018 | Kapadia et al. |
| 2018/0333213 | A1 | 11/2018 | Johnson et al. |
| 2018/0360546 | A1 | 12/2018 | Blumenkranz et al. |
| 2019/0000561 | A1 | 1/2019 | Decker et al. |
| 2019/0000569 | A1 | 1/2019 | Crawford et al. |
| 2019/0000580 | A1 | 1/2019 | Scheib et al. |
| 2019/0009416 | A1 | 1/2019 | Kalb et al. |
| 2019/0021795 | A1 | 1/2019 | Crawford et al. |
| 2019/0021799 | A1 | 1/2019 | Crawford et al. |
| 2019/0021800 | A1 | 1/2019 | Crawford et al. |
| 2019/0029737 | A1 | 1/2019 | Wall et al. |
| 2019/0029765 | A1 | 1/2019 | Crawford et al. |
| 2019/0039241 | A1 | 2/2019 | Langenfeld et al. |
| 2019/0046281 | A1 | 2/2019 | Johnson et al. |
| 2019/0046284 | A1 | 2/2019 | Pennoyer et al. |
| 2019/0053862 | A1 | 2/2019 | Ecke et al. |
| 2019/0053866 | A1 | 2/2019 | Seow et al. |
| 2019/0069961 | A1 | 3/2019 | Smith et al. |
| 2019/0069962 | A1 | 3/2019 | Tabandeh et al. |
| 2019/0069969 | A1 | 3/2019 | Higuchi et al. |
| 2019/0076204 | A1 | 3/2019 | Robertson et al. |
| 2019/0099232 | A1 * | 4/2019 | Soto ....................... A61B 46/10 |
| 2019/0117313 | A1 | 4/2019 | Crawford |
| 2019/0133790 | A1 | 5/2019 | Viscardi et al. |
| 2019/0133791 | A1 | 5/2019 | Yadav et al. |
| 2019/0142534 | A1 | 5/2019 | Cleary et al. |
| 2019/0142540 | A1 | 5/2019 | Chow |
| 2019/0150901 | A1 | 5/2019 | Ponzer et al. |
| 2019/0151040 | A1 | 5/2019 | Chua et al. |
| 2019/0167362 | A1 | 6/2019 | Crawford et al. |
| 2019/0167365 | A1 | 6/2019 | Chaplin et al. |
| 2019/0183594 | A1 | 6/2019 | Shelton, IV et al. |
| 2019/0192240 | A1 | 6/2019 | Mintz et al. |
| 2019/0216554 | A1 | 7/2019 | Kapadia |
| 2019/0223965 | A1 | 7/2019 | Marshall et al. |
| 2019/0223966 | A1 | 7/2019 | Holop et al. |
| 2019/0223969 | A1 | 7/2019 | Ramstad et al. |
| 2019/0223976 | A1 | 7/2019 | Krinninger et al. |
| 2019/0231448 | A1 | 8/2019 | McBrien et al. |
| 2019/0231455 | A1 | 8/2019 | Cooper et al. |
| 2019/0231464 | A1 | 8/2019 | Wixey et al. |
| 2019/0239969 | A1 | 8/2019 | Abu-Akeel et al. |
| 2019/0247134 | A1 | 8/2019 | Marinchak |
| 2019/0254763 | A1 | 8/2019 | Lambrecht et al. |
| 2019/0274766 | A1 | 9/2019 | Holop et al. |
| 2019/0274780 | A1 | 9/2019 | Nowatschin et al. |
| 2019/0282313 | A1 | 9/2019 | Devengenzo et al. |
| 2019/0282315 | A1 | 9/2019 | Loh et al. |
| 2019/0290378 | A1 | 9/2019 | Schwagli et al. |
| 2019/0290379 | A1 | 9/2019 | Flatt et al. |
| 2019/0298461 | A1 | 10/2019 | Holop et al. |
| 2019/0298469 | A1 | 10/2019 | Ramstad et al. |
| 2019/0298470 | A1 | 10/2019 | Ramstad et al. |
| 2019/0298471 | A1 | 10/2019 | Holop |
| 2019/0321120 | A1 | 10/2019 | Hutchison et al. |
| 2019/0328473 | A1 | 10/2019 | Chassot et al. |
| 2020/0000490 | A1 | 1/2020 | McGrogan et al. |
| 2020/0046207 | A1 | 2/2020 | Calavrezos et al. |
| 2020/0046394 | A1 | 2/2020 | Cau |
| 2020/0046442 | A1 | 2/2020 | Rogers et al. |
| 2020/0058284 | A1 | 2/2020 | Miller et al. |
| 2020/0061847 | A1 | 2/2020 | Dixon |
| 2020/0069383 | A1 | 3/2020 | Betsugi et al. |
| 2020/0069385 | A1 | 3/2020 | Ago et al. |
| 2020/0069386 | A1 | 3/2020 | Betsugi et al. |
| 2020/0069389 | A1 | 3/2020 | Morrissette et al. |
| 2020/0069390 | A1 | 3/2020 | Betsugi et al. |
| 2020/0093556 | A1 | 3/2020 | Zemlok et al. |
| 2020/0121400 | A1 | 4/2020 | Girardeau-Montaut et al. |
| 2020/0170724 | A1 | 6/2020 | Flatt et al. |
| 2020/0170740 | A1 | 6/2020 | Galili et al. |
| 2020/0179072 | A1 | 6/2020 | Pennoyer et al. |
| 2020/0188050 | A1 | 6/2020 | Pennoyer et al. |
| 2020/0205641 | A1 | 7/2020 | Luck et al. |

(56) References Cited

U.S. PATENT DOCUMENTS

| | | | |
|---|---|---|---|
| 2020/0205793 A1 | 7/2020 | Jang et al. | |
| 2020/0246082 A1 | 8/2020 | Malackowski et al. | |
| 2020/0261161 A1 | 8/2020 | Frielinghaus et al. | |
| 2021/0109834 A1 | 4/2021 | Singh et al. | |
| 2021/0330273 A1* | 10/2021 | Crawford | A61B 6/4441 |
| 2022/0008137 A1 | 1/2022 | Brik et al. | |
| 2022/0022970 A1 | 1/2022 | Li | |
| 2022/0184824 A1 | 6/2022 | Collet | |
| 2023/0397966 A1 | 12/2023 | Klann et al. | |
| 2023/0398966 A1 | 12/2023 | Kerber-Wunderlich et al. | |

FOREIGN PATENT DOCUMENTS

| | | | | |
|---|---|---|---|---|
| DE | 102012008535 A1 | 10/2013 | | |
| EP | 3569159 A1 * | 11/2019 | A61B 90/39 |
| GB | 2447239 A | 9/2008 | |
| GB | 2483154 A | 2/2012 | |
| GB | 2570514 A | 7/2019 | |
| GB | 2572333 A | 10/2019 | |
| WO | 2009092701 A1 | 7/2009 | |
| WO | 2009123891 A1 | 10/2009 | |
| WO | 2009123925 A1 | 10/2009 | |
| WO | 2010121107 A1 | 10/2010 | |
| WO | 2010121117 A1 | 10/2010 | |
| WO | 2011037394 A2 | 3/2011 | |
| WO | 2013075204 A1 | 5/2013 | |
| WO | 2013075205 A1 | 5/2013 | |
| WO | 2013159932 A1 | 10/2013 | |
| WO | 2014162217 A1 | 10/2014 | |
| WO | 2014165828 A1 | 10/2014 | |
| WO | 2015023834 A1 | 2/2015 | |
| WO | 2015052629 A1 | 4/2015 | |
| WO | 2015110542 A1 | 7/2015 | |
| WO | 2015142814 A1 | 9/2015 | |
| WO | 2015142815 A1 | 9/2015 | |
| WO | 2016028388 A1 | 2/2016 | |
| WO | 2016134266 A1 | 8/2016 | |
| WO | WO-2017044884 A1 * | 3/2017 | A61B 34/30 |
| WO | 2017144115 A1 | 8/2017 | |
| WO | 2017208186 A2 | 12/2017 | |
| WO | 2018111575 A1 | 6/2018 | |
| WO | 2018189729 A1 | 10/2018 | |
| WO | 2019023378 A1 | 1/2019 | |
| WO | 2019023383 A2 | 1/2019 | |
| WO | 2019023386 A2 | 1/2019 | |
| WO | 2019023390 A2 | 1/2019 | |
| WO | 2019023393 A1 | 1/2019 | |
| WO | 2019054880 A1 | 3/2019 | |
| WO | 2019071189 A2 | 4/2019 | |
| WO | 2019096933 A2 | 5/2019 | |
| WO | 2019108567 A1 | 6/2019 | |
| WO | 2019150086 A1 | 8/2019 | |
| WO | 2019150111 A1 | 8/2019 | |
| WO | 2019195841 A1 | 10/2019 | |

OTHER PUBLICATIONS

Bi, "Benjun et al., "The Effect of Robot-Navigation-Assisted Core Decompression on Early Stage Osteonecrosis of the Femoral Head, Journal of Orthopaedic Surgery and Research, https://josr-online.biomedcentral.com/articles/10.1186/s13018-019-1437-x, 2019, 9 pages.

Culpepper, Martin L. et al., "Design of Low-Cost Kinematic Couplings Using Formed Balls and Grooves in Sheet Metal Parts" Massachusetts Institute of Technology, Cambridge, MA, Oct. 2003, 4 pages.

English language abstract and machine-assisted English translation for CN 100464720 C extracted from espacenet.com database on Aug. 12, 2021, 42 pages.

English language abstract and machine-assisted English translation for DE 10 2012 008 535 extracted from espacenet.com database on Sep. 30, 2019, 36 pages.

English language abstract for WO 2011/037394 extracted from espacenet.com database on Apr. 20, 2020, 1 page.

English language abstract for WO 2013/159932 extracted from espacenet.com database on Apr. 20, 2020, 2 pages.

English language abstract for WO 2009/092701 A1 extracted from espacenet.com database on Apr. 20, 2020, 2 pages.

Furse, J.E., "Kinematic Design of Fine Mechanisms in Instruments", Instrument Science and Technology, Engineering Services, National Physical Laboratory, Teddington, Middlesex, UK, J. Phys. E: Sci. Instrum., vol. 14, 1981, 8 pages.

Hale, Layton C, , "Optimal Design Techniques for Kinematic Couplings", Lawrence Livermore National Laboratory, Livermore, CA, USA, Precision Engineering Journal of the International Societies for Precision Engineering and Nanotechnology, vol. 25, Oct. 5, 2000, pp. 114-127-.

International Search Report for Application No. PCT/US2016/018691 dated Jun. 1, 2016, 2 pages.

International Search Report for Application No. PCT/US2019/064429 dated Jul. 7, 2020, 3 pages.

Invitation to Pay Additional Fees/Partial International Search Report for Application No. PCT/US 2019/064429 dated Mar. 6, 2020, 3 pages.

Malti, Abed, "Robust Hand-Eye Calibration for Computer Aided Medical Endoscopy", IEEE International Conference on Robotics and Automation, May 2010, 8 pages.

O'Brien, Robert, "Visualizing Rank Deficient Models: A Row Equation Geometry of Rank Deficient Mateices and Constrained-Regression", PLOS ONE, Jun. 19, 2012, 12 pages.

Pharr, Matt et al., "Quaternion Multiplication—Geometry and Transformations", ScienceDirect, 2017, 14 pages.

Slocum, Alexander H., "Design of Three-Groove Kinematic Couplings", Department of Mechanical Engineering, Massachusetts Institute of Technology, Cambridge, MA, USA, Butterworth-Heinemann, 1992, 10 pages.

Stapel, Elizabeth, "Matrix Inversion: Finding the Inverse of a Matrix", Purplemath, https://www.purplemath.com/modules/mtrxinvr.htm, Jun. 2020, 2 pages.

Stryker, "MAKO PKA Application User Guide", https://www.strykermeded.com/media/2943/mako-pka-application-user-guide-pka-30-003.pdf, 2020, 108 pages.

Widnall, S., "Lecture L3—Vectures, Matrices and Coordinate Transformations", 16.07 Dynamics, Lecture Notes based on J. Peraire Version 2.0, Fall 2009, 16 pages.

Wikipedia, "Rotation Matrix", May 2020, 25 pages.

* cited by examiner $A_1 X B_1$ = Transorm from LCLZ to MNPL at time $t_1$ $A_2 X B_2$ = Transorm from LCLZ to MNPL at time $t_2$ $$\underbrace{A_2^{-1} A_1}_{A} X = X \underbrace{B_2^{-1} B_1}_{B}$$

Solve for X by addressing rotation and translation separately:

General equation is an equivalence of two transform chains:

$$AX = XB$$

Transform math:

$$\begin{bmatrix} R_A & t_A \\ 0 & 1 \end{bmatrix} \begin{bmatrix} R_X & t_X \\ 0 & 1 \end{bmatrix} = \begin{bmatrix} R_X & t_X \\ 0 & 1 \end{bmatrix} \begin{bmatrix} R_B & t_B \\ 0 & 1 \end{bmatrix}$$

General equations describing rotation and translation relationships used to solve x:

① $R_A R_X = R_X R_B$ Governing Rotation Equation and

② $R_A \vec{t}_X + \vec{t}_A = R_X \vec{t}_B + \vec{t}_X$ Governing Translation Equation

FIG. 14

① $R_A R_X = R_X R_B$

The rotation portion of the problem comprises these steps:

- Re-express rotations as unit quaternions
- Reorganize the algebraic expression into the format KX=0
- Utilize a Singular Value Decomposition to find the vector, x which lies in the null space of the rank deficient K matrix (non-trivial solution for x)
- Vector x re-expressed as a rotation matrix instead of a unit quaternion

FIG. 15

FIG. 17 Translation Portion

With Rx resolved, reoranize the second governing equation:

$$\textcircled{2}\quad R_A\vec{t}_X + \vec{t}_A = R_X\vec{t}_B + \vec{t}_X$$

$$R_A\vec{t}_X - \vec{t}_X = R_X\vec{t}_B - \vec{t}_A$$

$$\underbrace{[R_A - I_3]}_{\text{KNOWN}}\ \underbrace{\vec{t}_X}_{\text{UNKNOWN}} = \underbrace{R_X\vec{t}_B - \vec{t}_A}_{\text{KNOWN}}$$

FIG. 18 The Final Transform

The final transformation matrix describing the flange coordinate system FLG in terms of tracker coordinate system TRK1 is as follows:

$$\begin{bmatrix} R_X & \vec{t}_X \\ 0 & 1 \end{bmatrix}$$

ROBOTIC SURGICAL SYSTEM INCLUDING A COUPLER FOR CONNECTING A TOOL TO A MANIPULATOR AND METHODS OF USING THE COUPLER

CROSS-REFERENCE TO RELATED APPLICATIONS

The subject application claims priority to and all the benefits from U.S. Provisional Patent Application No. 63/061,266, filed Aug. 5, 2020, the entire contents of which are hereby incorporated by reference.

TECHNICAL FIELD

The present disclosure relates generally to robotic surgical systems including a coupler for connecting a tool to a manipulator and methods of using the coupler.

BACKGROUND

Robotic surgical systems are performing more and more surgical procedures each year. A typical robotic surgical system includes a robotic manipulator and a tool coupled to the manipulator. Often, the tool removes tissue from a patient at a surgical site. The robotic surgical system may include a navigation system that provides information relating to the pose of the tool relative to the surgical site so that the manipulator can precisely control movement of the tool relative to the surgical site. The navigation system includes trackers placed on the patient and on the manipulator and a localizer that cooperates with the trackers to locate the tool in relation to the surgical site. When optical localization methods are employed, if one or more of the trackers are blocked from view of the localizer, then errors in tracking the pose of the tool relative to the surgical site can occur. Accordingly, robotic surgical systems are desired that mitigate or reduce such errors associated with the trackers being outside of the field-of-view of the localizer.

SUMMARY

This Summary introduces a selection of concepts in a simplified form that are further described below in the Detailed Description below. This Summary is not intended to limit the scope of the claimed subject matter nor identify key features or essential features of the claimed subject matter.

In a first aspect, a robotic surgical system is provided for use with a localizer. The robotic surgical system comprises a robotic manipulator, a drape, a tool, and a coupler. The manipulator includes a plurality of links and a plurality of joints, wherein one of the plurality of links is a distal link that includes a first mounting interface having a plurality of first mounting elements. The drape is shaped to be disposed over the manipulator. The tool includes a second mounting interface having a plurality of second mounting elements. The coupler is connectable to the first mounting interface of the distal link and is connectable to the second mounting interface of the tool. The coupler includes a tracker to be detected by the localizer to determine a pose of the tool. The coupler is configured to cooperate with the drape to create a sterile field barrier between the tool and the robotic manipulator. The coupler includes a first coupling interface having a plurality of first coupling elements arranged to align with and engage the first mounting elements when connecting the coupler to the distal link. The coupler also includes a second coupling interface having a plurality of second coupling elements arranged to align with and engage the second mounting elements when connecting the coupler to the tool.

In a second aspect, a robotic surgical system is provided for use with a localizer. The robotic surgical system comprises a manipulator, a coupler, and a tool. The manipulator includes a first mounting interface. The coupler includes a first coupling interface, a second coupling interface, and a tracker to be detected by the localizer. The first coupling interface is connectable to the first mounting interface. The tool includes a second mounting interface selectively connectable to the second coupling interface and the first mounting interface.

In a third aspect, a coupler is provided for use with a drape to create a sterile field barrier between a tool and a robotic manipulator, wherein the robotic manipulator includes a first mounting interface having a plurality of first mounting elements and the tool includes a second mounting interface having a plurality of second mounting elements. The second mounting interface is connectable to the first mounting interface. The coupler comprises a coupler body, a first coupling interface, a second coupling interface, and a tracker. The first coupling interface is integrated with the coupler body and is connectable to the first mounting interface. The second coupling interface is integrated with the coupler body and is connectable to the second mounting interface. The tracker is coupled to the coupler body to be detected by a localizer. The first coupling interface has a plurality of first coupling elements arranged to align with and engage the first mounting elements when connecting the coupler to the robotic manipulator. The coupler also includes a second coupling interface having a plurality of second coupling elements arranged to align with and engage the second mounting elements when connecting the coupler to the tool.

In a fourth aspect, a robotic surgical system is provided for use with a localizer. The robotic surgical system comprises a robotic manipulator, a tool, a coupler, and a drape. The manipulator includes a first mounting interface. The tool includes a second mounting interface. The coupler is connectable to the first mounting interface of the robotic manipulator and is connectable to the second mounting interface of the tool. The coupler includes a tracker to be detected by the localizer to determine a pose of the tool. The drape is connectable to the coupler and is shaped to be disposed over the manipulator. The coupler is configured to cooperate with the drape to create a sterile field barrier between the tool and the robotic manipulator.

In a fifth aspect, a method of tracking a tool using a coupler is provided. The coupler includes a tracker. The coupler interconnects the tool and a robotic manipulator. The method comprises disposing a drape about a first mounting interface of the robotic manipulator and disposing the drape over one or more links of the robotic manipulator. The first mounting interface includes a plurality of first mounting elements. The method also comprises attaching the coupler to the first mounting interface to at least partially cover the first mounting interface, wherein the tracker can be detected by the localizer to determine a pose of the tool. The method also comprises attaching the tool to the coupler, wherein the coupler is configured to cooperate with the drape to create a sterile field barrier between the tool and the robotic manipulator. The tool includes a second mounting interface including a plurality of second mounting elements. Attaching the coupler to the first mounting interface includes aligning and engaging a plurality of first coupling elements with the first mounting elements and attaching the tool to the coupler includes aligning and engaging a plurality of second coupling elements with the second mounting elements.

In a sixth aspect, a surgical system is provided for use with a localizer. The surgical system comprises an arm, a drape shaped to be disposed over the arm, a tool, and a coupler. The arm includes a plurality of links and a plurality of joints, wherein one of the plurality of links is a distal link that includes a first mounting interface having a plurality of first mounting elements. The tool includes a second mounting interface having a plurality of second mounting elements. The coupler is connectable to the first mounting interface and the second mounting interface. The coupler is configured to cooperate with the drape to create a sterile field barrier between the tool and the arm. The coupler includes a tracker to be detected by the localizer to determine a pose of the tool. The coupler includes a first coupling interface having a plurality of first coupling elements arranged to align with and engage the first mounting elements when connecting the coupler to the distal link. The coupler also includes a second coupling interface having a plurality of second coupling elements arranged to align with and engage the second mounting elements when connecting the coupler to the tool.

In a seventh aspect, a robotic surgical system is provided for use with a localizer. The robotic surgical system comprises a robotic manipulator, a drape shaped to be disposed over the robotic manipulator, a tool, and a coupler. The robotic manipulator includes a plurality of links and a plurality of joints, wherein one of the plurality of links is a distal link that includes a first mounting interface. The tool includes a second mounting interface. The coupler is connectable to the first mounting interface and to the second mounting interface. The coupler is configured to cooperate with the drape to create a sterile field barrier between the tool and the robotic manipulator. The coupler includes a tracker to be detected by the localizer to determine a pose of the tool. The coupler includes a plurality of kinematic coupling elements and each of the first and second mounting interfaces include a plurality of kinematic mounting elements shaped to engage the plurality of kinematic coupling elements so that exactly six degrees of freedom is constrained between the tool and the robotic manipulator.

In an eighth aspect, a robotic surgical system is provided for use with a localizer, the robotic surgical system comprising: a first tool comprising a distal tip and a first tracker detectable by the localizer to determine a pose of the first tool; a robotic manipulator including a first mounting interface; a second tool for mounting to the robotic manipulator and including a second mounting interface; and a coupler connectable between the first mounting interface and the second mounting interface to mount the second tool to the robotic manipulator, and wherein the coupler includes: a second tracker detectable by the localizer to determine a pose of the second tool; and a checkpoint feature configured to be interfaced with by the distal tip of the first tool to facilitate verification of one or more components of the robotic surgical system.

In a ninth aspect, a surgical system for use with a localizer, the surgical system comprising: a robotic manipulator or mechanical linkage including a first mounting interface; a second tool including a second mounting interface; and a coupler connectable between the first mounting interface and the second mounting interface to mount the second tool to the robotic manipulator or mechanical linkage, and wherein the coupler includes a tracker detectable by the localizer to determine a pose of the tool, wherein the tracker is positionable in different orientations on the coupler.

Systems, methods of use, and subcomponents of any of the above-aspects are contemplated.

For any of the above aspects, individually or in combination, at least any of the following implementations are possible:

In one implementation, the coupler includes a first side and an opposing second side. In one implementation, the first coupling interface is arranged on the first side to connect to the first mounting interface. In one implementation, the second coupling interface is arranged on the second side to connect to the second mounting interface. In one implementation, the coupler has a generally cylindrical shape. In one implementation, the first and second sides are geometrically opposing sides of the coupler and are substantially parallel to one another.

In one implementation, the second mounting interface is connectable to the second coupling interface in at least two different orientations, and optionally, in multiple orientations within a 360-degree range.

In one implementation, the coupler includes a coupler body, the first and second coupling interfaces being integrated with the coupler body. In one implementation, the coupling interfaces are detachable from the coupler body. In one implementation, first and second coupling interfaces are located on opposing sides of the coupler body.

In one implementation, the tracker is connectable to the coupler body in at least two different orientations, and optionally, in multiple orientations within a 360-degree range. In one implementation, the tracker has a tracker body for supporting tracking elements. In one implementation, wherein the tracker body is integrally formed with the coupler body. In one implementation, the tracker body is connectable to the coupler body. In one implementation, the tracking elements are any one or more of: optical, retroreflective, active and/or passive infrared tracking elements. In one implementation, the tracker is integrally formed with the coupler body. In another implementation, the tracker (or tracker parts) is detachable from/attachable to the coupler body. In one implementation, the tracker (or tracker parts) or coupler body are reusable or sterilizable. In one implementation, the tracker (or tracker parts) is single use and disposable.

In one implementation, the second mounting interface is connectable to the first mounting interface.

In one implementation, the plurality of second mounting elements are shaped and arranged to engage the plurality of first mounting elements when connecting the second mounting interface to the first mounting interface. In one implementation, the plurality of first coupling elements are shaped to engage, by surface contact, the plurality of first mounting elements of the first mounting interface when connecting the first coupling interface to the first mounting interface. In one implementation, the plurality of second coupling elements are shaped to engage, by surface contact, the plurality of second mounting elements when connecting the second coupling interface to the second mounting interface.

In one implementation, the plurality of first coupling elements includes a flat block and a V-shaped block and the plurality of second coupling elements includes a pair of semi-cylindrically shaped surfaces. In one implementation, the plurality of second coupling elements includes a flat block and a V-shaped block and the plurality of first coupling elements includes a pair of semi-cylindrically shaped surfaces.

In one implementation, the plurality of first coupling elements include first kinematic coupling elements and the plurality of second coupling elements include second kinematic coupling elements.

In one implementation, the coupler and the drape are further defined as a sterile coupler and a sterile drape. In one implementation, the coupler and the drape are sterilized components.

In one implementation, the drape is connectable to the coupler. In one implementation, the distal link includes a first mounting flange that includes the first mounting interface and the drape is shaped to be disposed between the first mounting flange and the coupler.

In one implementation, disposing the drape about the first mounting interface of the robotic manipulator includes disposing a ring of the drape about the first mounting interface and over a mounting flange of the robotic manipulator.

In one implementation, disposing the drape over the one or more links of the robotic manipulator includes disposing a covering portion of the drape over the one or more links of the robotic manipulator.

In one implementation, attaching the coupler to the first mounting interface to at least partially cover the first mounting interface includes attaching the coupler to the first mounting interface so that the ring of the drape is captured between the mounting flange and the coupler to create the sterile field barrier between the tool and the robotic manipulator.

Any of the above aspects can be combined in full or in part. Any features of the above aspects can be combined in full or in part. Any of the above implementations for any aspect can be combined with any other aspect. Any of the above implementations can be combined with any other implementation whether for the same aspect or different aspect.

DESCRIPTION OF THE DRAWINGS

Advantages of the present disclosure will be readily appreciated as the same becomes better understood by reference to the following detailed description when considered in connection with the accompanying drawings.

FIGS. 14 through 18 illustrate an algorithm through which the transform is calculated, according to one implementation.

DETAILED DESCRIPTION

Figure 1:
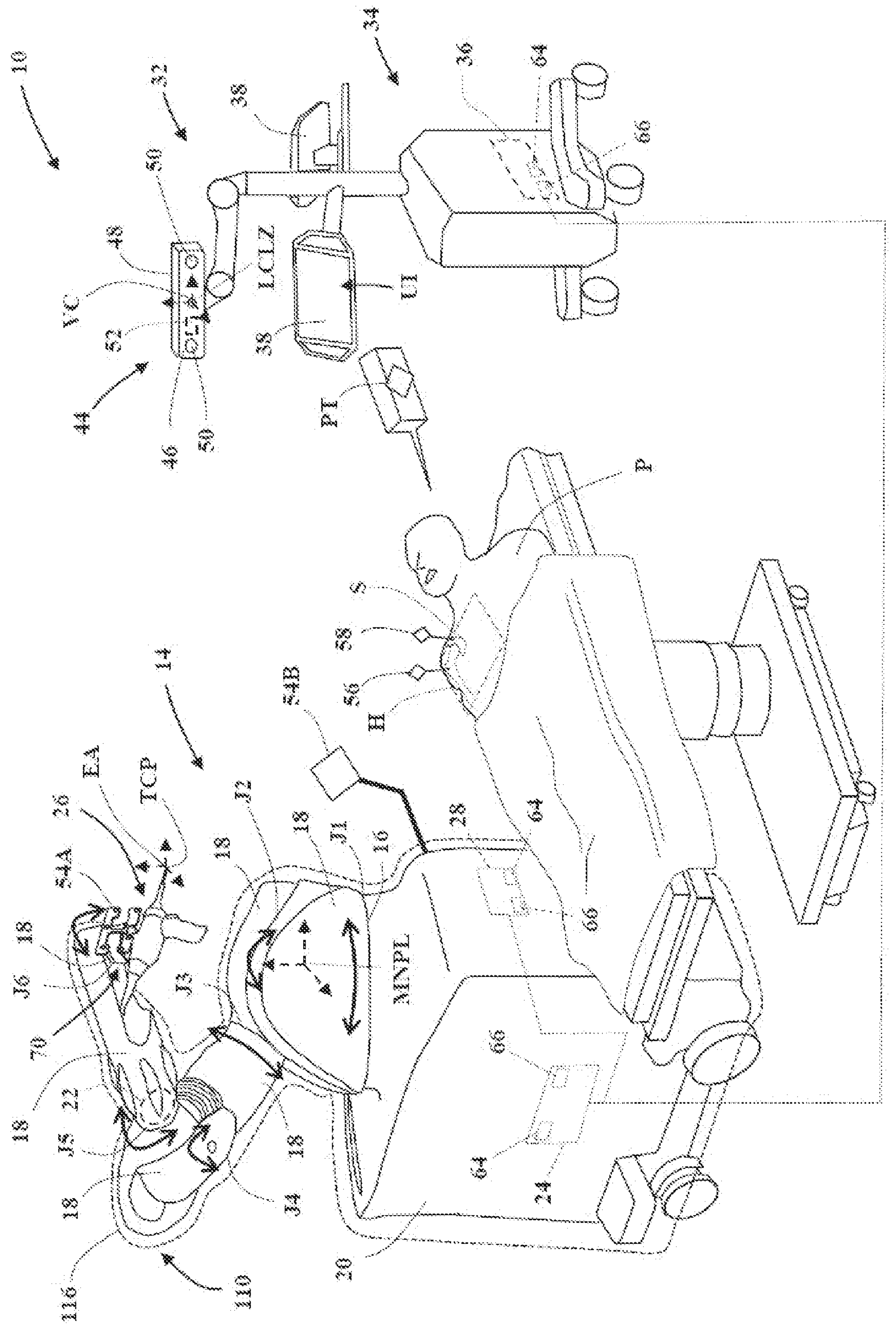
FIG. 1 is a perspective view of a robotic surgical system, according to one implementation.

Referring to FIG. 1, a robotic surgical system 10 is illustrated. The system 10 is useful for treating a surgical site or anatomical volume of a patient P, such as treating bone or soft tissue. In FIG. 1, the patient P is undergoing a surgical procedure. The surgical procedure may involve tissue removal or other forms of treatment. Treatment may include cutting, coagulating, lesioning the tissue, other in-situ tissue treatments, or the like. In some examples, the surgical procedure involves shoulder replacement surgery, partial or total knee or hip replacement surgery, spine surgery, or ankle surgery. In some examples, the system 10 is designed to cut away material to be replaced by surgical implants, such as shoulder implants, partial or total knee implants, hip implants, spine implants, or ankle implants. In FIG. 1, the system 10 is shown being employed to prepare the humerus H and/or a glenoid cavity of a scapula S to receive shoulder implants. Examples of shoulder implants, and methods of implanting them, are shown in U.S. Patent Application Publication No. 2019/0133790, filed on Nov. 6, 2018, entitled, “Robotic System For Shoulder Arthroplasty Using Stemless Implant Components,” and U.S. Patent Application Publication No. 2019/0133791, filed on Nov. 6, 2018, entitled, “Robotic System For Shoulder Arthroplasty Using Stemless Implant Components,” the disclosures of both of which are hereby incorporated herein by reference. The system 10 and techniques disclosed herein may be used to perform other procedures, surgical or non-surgical, or may be used in industrial applications or other applications where robotic systems are utilized.

The system 10 includes a manipulator 14. The manipulator 14 has a base 16 and plurality of links 18. A manipulator cart 20 can support the manipulator 14 such that the manipulator 14 is fixed to the manipulator cart 20. In other examples, the manipulator 14 can be mounted to a surgical patient table. The links 18 collectively form one or more arms or linkages of the manipulator 14 with adjacent links being connected by joints. The manipulator 14 may have a serial, robotic arm configuration (as shown in FIG. 1), a parallel, robotic arm configuration, or any other suitable manipulator configuration. In other examples, more than one manipulator 14 may be utilized in a multiple arm configuration.

In the example shown in FIG. 1, the manipulator 14 comprises a plurality of joints J1-J6 and a plurality of joint encoders 22 located at the joints J1-J6 for determining position data (e.g., rotation angles) of the joints J1-J6. For simplicity, only one joint encoder 22 is illustrated in FIG. 1, although other joint encoders 22 may be similarly illustrated. The manipulator 14 according to one example has six joints J1-J6 implementing at least six-degrees of freedom (DOF) for the manipulator 14. However, the manipulator 14 may have any number of degrees of freedom and may have any suitable number of joints J and may have redundant joints.

The manipulator 14 need not require joint encoders 22 but may alternatively, or additionally, utilize motor encoders present on motors at each joint J. Also, the manipulator 14 need not require rotary joints, but may alternatively, or additionally, utilize one or more prismatic joints. Any suitable combination of joint types are contemplated. The manipulator 14 may be the manipulator currently used in the Mako robotic system manufactured by Mako Surgical Corp., a subsidiary of Stryker Corporation.

The base 16 of the manipulator 14 is generally a portion of the manipulator 14 that provides a fixed reference coordinate system for other components of the manipulator 14 or the system 10 in general. Generally, the origin of a manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 20, such as where the manipulator 14 is physically attached to the cart 20. In one example, the base 16 is defined at an intersection of the axes of joints J1 and J2. Thus, although joints J1 and J2 are moving components in reality, the intersection of the axes of joints J1 and J2 is nevertheless a virtual fixed reference pose, which provides both a fixed position and orientation reference and which does not move relative to the manipulator 14 and/or manipulator cart 20. In other examples, the manipulator 14 can be a hand-held manipulator where the base 16 is a base portion of a tool (e.g., a portion held free-hand by the user) and the tool tip is movable relative to the base portion. The base portion has a reference coordinate system that is tracked and the tool tip has a tool tip coordinate system that is tracked relative to the reference coordinate system.

The manipulator 14 and/or manipulator cart 20 house a manipulator controller 24, or other type of control unit. The manipulator controller 24 may comprise one or more computers, or any other suitable form of controller that directs the motion of the manipulator 14. The manipulator controller 24 may have a central processing unit (CPU) and/or other processors, memory (not shown), and storage (not shown). The manipulator controller 24 is loaded with software as described below. The processors could include one or more processors to control operation of the manipulator 14. The processors can be any type of microprocessor, multi-processor, and/or multi-core processing system. The manipulator controller 24 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor. The manipulator 14 may also comprise a user interface UI (see FIG. 2) with one or more displays and/or input devices (e.g., push buttons, keyboard, mouse, microphone (voice-activation), gesture control devices, touchscreens, etc.).

A surgical tool 26 couples to the manipulator 14 and is movable relative to the base 16 to interact with the anatomy in certain modes. The tool 26 is or forms part of an end effector supported by the manipulator 14 in certain embodiments. The tool 26 may be grasped by the user. One possible arrangement of the manipulator 14 and the tool 26 is described in U.S. Pat. No. 9,119,655, entitled, "Surgical Manipulator Capable Of Controlling A Surgical Tool In Multiple Modes," filed on Aug. 2, 2013, the disclosure of which is hereby incorporated herein by reference. The manipulator 14 and the tool 26 may be arranged in alternative configurations. The tool 26 can be like that shown in U.S. Patent Application Publication No. 2014/0276949, filed on Mar. 15, 2014, entitled, "End Effector Of A Surgical Robotic Manipulator," hereby incorporated herein by reference.

Figure 3:
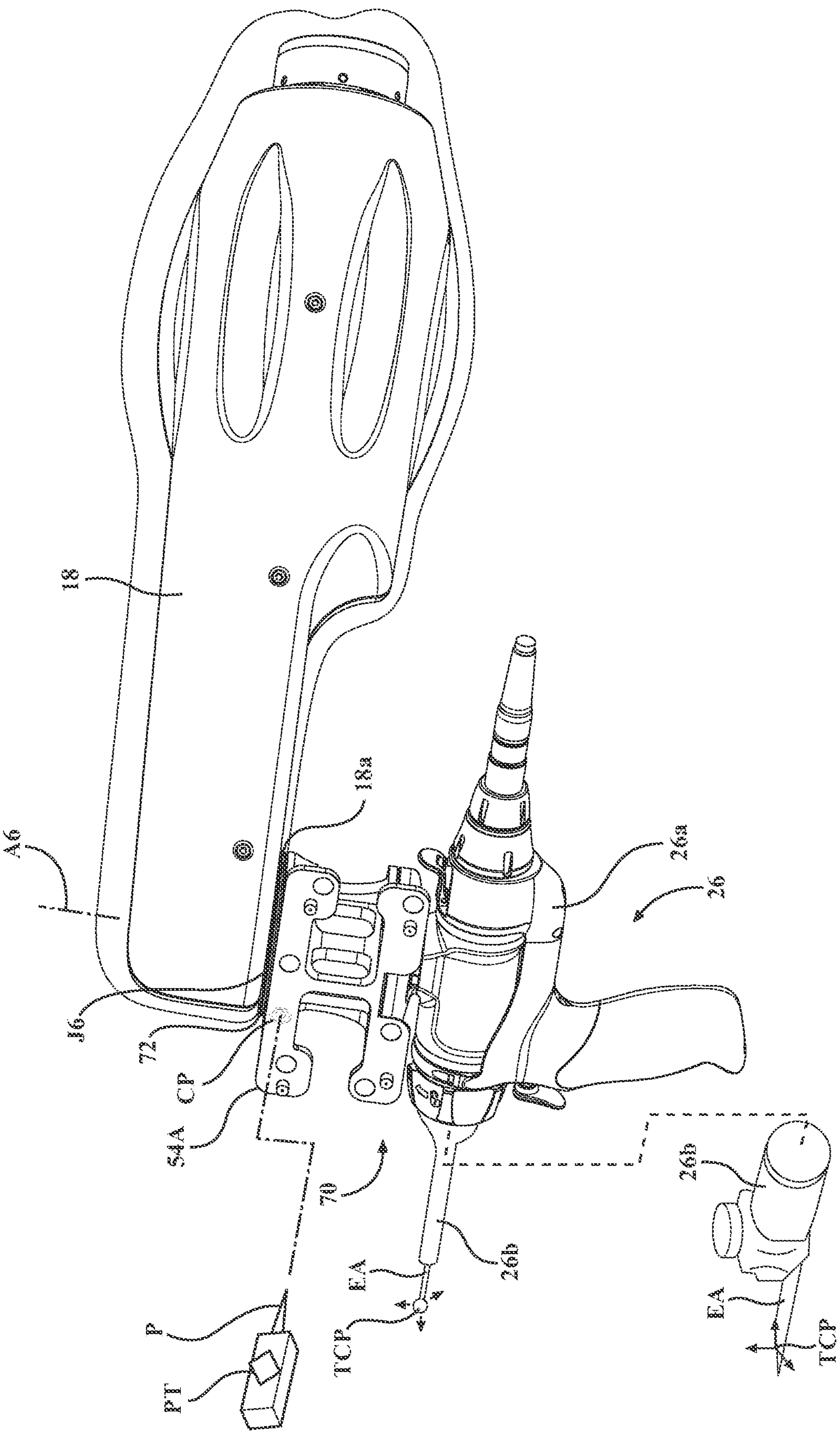
FIG. 3 is a perspective view of a distal link of a robotic manipulator and a sterile coupler connecting a tool to the distal link, according to one implementation.

The tool 26 includes an energy applicator EA designed to contact and remove the tissue of the patient P at the surgical site. In one example, the energy applicator EA is a burr. The burr may be substantially spherical and comprise a spherical center, radius (r) and diameter. Alternatively, the energy applicator EA may be a drill bit, a saw blade, an ultrasonic vibrating tip, or the like. In some versions, the tool 26 includes non-motorized accessories such as a probe, a retractor, a cutting guide, or the like. The tool 26 and/or energy applicator EA/accessory may comprise any geometric feature, e.g., perimeter, circumference, radius, diameter, width, length, volume, area, surface/plane, range of motion envelope (along any one or more axes), etc. The geometric feature may be considered to determine how to locate the tool 26 relative to the tissue at the surgical site to perform the desired treatment. In some of the embodiments described herein, a spherical burr having a tool center point (TCP) will be described for convenience and ease of illustration but is not intended to limit the tool 26 to any particular form. In the version shown, the tool 26 comprises a tool driver 26*a* (see FIG. 3) that houses any driving motor for the energy applicator EA, e.g., to drive saw blade oscillation, burr rotation, drill rotation, etc. The tool 26 also comprises a tool holder 26*b* that releasably connects to the tool driver 26*a* to interchange different energy applicators EA. The tool holder 26*b* releasably holds the energy applicator EA. The tool holder 26*b* can be releasably connected to the tool driver 26*a* using any suitable type of connection, e.g. snap-fit connection, bayonet-type connection, fasteners, collet connections, or the like. An example of two different tool holders 26*b* is shown in FIG. 3, one for a burr and one for a saw blade.

The tool 26 may comprise a tool controller 28 to control operation of the tool 26, such as to control power to the tool (e.g., to a rotary, driving motor of the tool 26), control movement of the tool 26, control irrigation/aspiration of the tool 26, and/or the like. The tool controller 28 may be in communication with the manipulator controller 24 or other components. The tool 26 may also comprise a user interface UI with one or more displays and/or input devices (e.g., push buttons, keyboard, mouse, microphone (voice-activation), gesture control devices, touchscreens, etc.). The manipulator controller 24 controls a state (e.g., position and/or orientation) of the tool 26 (e.g., the TCP) with respect to a coordinate system, such as the manipulator coordinate system MNPL. The manipulator controller 24 can control (linear or angular) velocity, acceleration, or other derivatives of motion of the tool 26.

The tool center point (TCP), in one example, is a predetermined reference point or coordinate system defined at the energy applicator EA. The TCP has a known, or able to be calculated (i.e., not necessarily static), pose relative to other coordinate systems. The geometry of the energy applicator EA is known in or defined relative to a TCP coordinate system. The TCP may be located at the spherical center of the burr of the tool 26 such that only one point is tracked.

The TCP may be defined in various ways depending on the configuration of the energy applicator EA. The manipulator 14 could employ the joint/motor encoders, or any other non-encoder position sensing method, to enable a pose of the TCP to be determined. The manipulator 14 may use joint measurements to determine TCP pose and/or could employ techniques to measure TCP pose directly. The control of the tool 26 is not limited to a center point. For example, any suitable primitives, meshes, etc., can be used to represent the tool 26.

The system 10 further includes a navigation system 32. One example of the navigation system 32 is described in U.S. Pat. No. 9,008,757, filed on Sep. 24, 2013, entitled, "Navigation System Including Optical And Non-Optical Sensors," hereby incorporated herein by reference. The navigation system 32 tracks movement of various objects. Such objects include, for example, the manipulator 14, the tool 26 and the anatomy, e.g., the humerus H and scapula S. The navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformations.

The navigation system 32 includes a cart assembly 34 that houses a navigation controller 36, and/or other types of control units. A navigation user interface UI is in operative communication with the navigation controller 36. The navigation user interface includes one or more displays 38. The navigation system 32 is capable of displaying a graphical representation of the relative states of the tracked objects to the user using the one or more displays 38. The navigation user interface UI further comprises one or more input devices to input information into the navigation controller 36 or otherwise to select/control certain aspects of the navigation controller 36. Such input devices include interactive touchscreen displays. However, the input devices may include any one or more of push buttons, a keyboard, a mouse, a microphone (voice-activation), gesture control devices, and the like.

The navigation system 32 also includes a navigation localizer 44 coupled to the navigation controller 36. In one example, the localizer 44 is an optical localizer and includes a camera unit 46. The camera unit 46 has an outer casing 48 that houses one or more optical sensors 50. The localizer 44 may include its own localizer controller 52 and may further include a video camera VC.

The navigation system 32 includes one or more trackers. In one example, the trackers include a pointer tracker PT, one or more tool or manipulator trackers 54A, 54B, a first patient tracker 56, and a second patient tracker 58. In the illustrated example of FIG. 1, one tool tracker 54A is fixed with respect to the tool 26, the first patient tracker 56 is firmly affixed to the humerus H of the patient P, and the second patient tracker 58 is firmly affixed to the scapula S of the patient P. In this example, the patient trackers 56, 58 are firmly affixed to sections of bone. The pointer tracker PT is firmly affixed to a pointer used for registering the anatomy to the localizer coordinate system LCLZ. The manipulator tracker 54B may be affixed to any suitable component of the manipulator 14, in addition to, or other than the tool 26, such as the base 16, the cart 20, or any one or more links 18 of the manipulator 14. The trackers 54A, 54B, 56, 58, PT may be fixed to their respective components in any suitable manner. For example, the trackers may be rigidly fixed, flexibly connected (optical fiber), or not physically connected at all (ultrasound), as long as there is a suitable (supplemental) way to determine the relationship (measurement) of that respective tracker to the object that it is associated with. In some cases, only one of the tool and manipulator trackers 54A, 54B are used, or both the tool and manipulator trackers 54A, 54B may be used.

In the illustrated embodiment, the trackers 54A, 54B, 56, 58, PT are passive trackers. Accordingly, each tracker 54A, 54B, 56, 58, PT has at least three passive tracking elements or markers M, such as reflectors, for reflecting light from the localizer 44 back to the optical sensors 50. In other embodiments, the trackers 54A, 54B, 56, 58, PT are active trackers and may have light emitting diodes or LEDs transmitting light, such as infrared light to the optical sensors 50. Based on the received optical signals, navigation controller 36 generates data indicating the relative positions and orientations of the trackers 54A, 54B, 56, 58, PT relative to the localizer 44 using conventional triangulation techniques. In some cases, more or fewer markers may be employed. For instance, in cases in which the object being tracked is rotatable about a line, two markers can be used to determine an orientation of the line by measuring positions of the markers at various locations about the line. It should be appreciated that the localizer 44 and trackers 54A, 54B, 56, 58, PT, although described above as utilizing optical tracking techniques, could alternatively, or additionally, utilize other tracking modalities to track the objects, such as electromagnetic tracking, radio frequency tracking, inertial tracking, ultrasound-based tracking, fiber-optic tracking, machine-vision tracking, combinations thereof, and the like.

The localizer 44 tracks the trackers 54A, 54B, 56, 58, PT to determine a state of each of the trackers 54A, 54B, 56, 58, PT, which correspond respectively to the state of the object respectively attached thereto. The localizer 44 provides the state of the trackers 54A, 54B, 56, 58, PT to the navigation controller 36. In one example, the navigation controller 36 determines and communicates the state of the trackers 54A, 54B, 56, 58, PT to the manipulator controller 24. As used herein, the state of an object includes, but is not limited to, data that defines the position and/or orientation of the tracked object or equivalents/derivatives of the position and/or orientation. For example, the state may be a pose of the object, and may include linear velocity data, and/or angular velocity data, and the like.

The navigation controller 36 may comprise one or more computers, or any other suitable form of controller. Navigation controller 36 has a central processing unit (CPU) and/or other processors, memory (not shown), and storage (not shown). The processors can be any type of processor, microprocessor or multi-processor system. The navigation controller 36 is loaded with software. The software, for example, converts the signals received from the localizer 44 into data representative of the position and orientation of the objects being tracked. The navigation controller 36 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor.

In operation, for certain surgical tasks, the user manually manipulates (e.g., moves or causes the movement of) the tool 26 to perform the surgical procedure on the patient, such as drilling, cutting, sawing, reaming, implant installation, and the like. As the user manipulates the tool 26, the navigation system 32 tracks the location of the tool 26 and/or the manipulator 14 and provides haptic feedback (e.g., force feedback) to the user to limit the user's ability to move (or cause movement of) the tool 26 beyond one or more predefined virtual boundaries that are registered (or mapped) to the patient's anatomy, which results in highly accurate and repeatable drilling, cutting, sawing, reaming, and/or implant placement.

In some embodiments, the manipulator 14 operates in a passive manner and provides haptic feedback when the surgeon attempts to move the tool 26 beyond the virtual boundary. The haptic feedback (e.g., a form of stereotactic feedback) is generated by one or more actuators (e.g., joint motors) of the manipulator 14 and transmitted to the user via a flexible transmission, such as a cable drive transmission. When the manipulator 14 is not providing haptic feedback, the manipulator 14 is freely moveable by the user. In some embodiments, like that shown in U.S. Pat. No. 9,566,122, incorporated herein by reference, the manipulator 14 is manipulated by the user in a similar manner, but the manipulator 14 operates in an active manner. For instance, the user applies force to the tool 26, which is measured by a force/torque sensor S (see FIG. 2), and the manipulator 14 emulates the user's desired movement based on measurements from the force/torque sensor S. For other surgical tasks, the manipulator 14 may operate autonomously.

Figure 2:
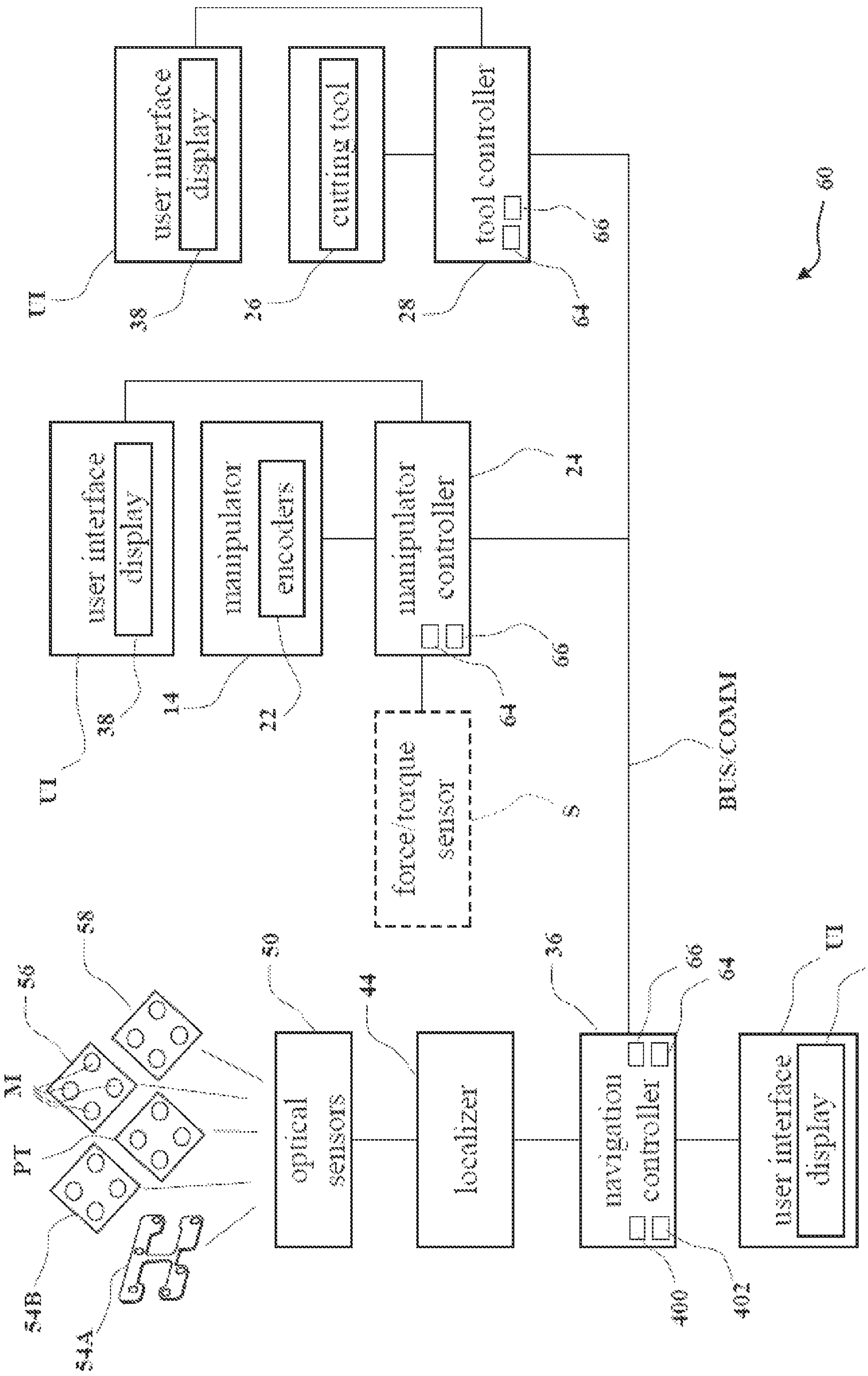
FIG. 2 is a block diagram of a control system for controlling the robotic surgical system, according to one implementation.

Referring to FIG. 2, the system 10 includes a control system 60 that comprises, among other components, the manipulator controller 24, the navigation controller 36, and the tool controller 28. The control system 60 further includes one or more software programs and software modules. The software modules may be part of the program or programs that operate on the manipulator controller 24, navigation controller 36, tool controller 28, or any combination thereof, to process data to assist with control of the system 10. The software programs and/or modules include computer readable instructions stored in non-transitory memory 64 on the manipulator controller 24, navigation controller 36, tool controller 28, or a combination thereof, to be executed by one or more processors 66 of the controllers 24, 28, 36. The memory 64 may be any suitable configuration of memory, such as RAM, non-volatile memory, etc., and may be implemented locally or from a remote database. Additionally, software modules for prompting and/or communicating with the user may form part of the program or programs and may include instructions stored in memory 64 on the manipulator controller 24, navigation controller 36, tool controller 28, or any combination thereof. The user may interact with any of the input devices of the navigation user interface UI or other user interface UI to communicate with the software modules. The user interface software may run on a separate device from the manipulator controller 24, navigation controller 36, and/or tool controller 28.

The control system 60 may comprise any suitable configuration of input, output, and processing devices suitable for carrying out the functions and methods described herein. The control system 60 may comprise the manipulator controller 24, the navigation controller 36, or the tool controller 28, or any combination thereof, or may comprise only one of these controllers. These controllers may communicate wirelessly, via a bus as shown in FIG. 2, or otherwise. The control system 60 may also be referred to as a controller. The control system 60 may comprise one or more microcontrollers, field programmable gate arrays, systems on a chip, discrete circuitry, sensors, displays, user interfaces, indicators, and/or other suitable hardware, software, or firmware that is capable of carrying out the functions described herein.

The manipulator controller 24 and/or the navigation controller 36 track the state of the tool 26 relative to the anatomy and the virtual boundaries. In one example, the state of the TCP is measured relative to the virtual boundaries for purposes of determining haptic forces to be applied to a virtual rigid body model via a virtual simulation so that the tool 26 remains in a desired positional relationship to the virtual boundaries (e.g., not moved beyond them, kept within them, etc.). The results of the virtual simulation are commanded to the manipulator 14.

In some embodiments, using the navigation system 32, the pose of the tool 26 can be determined by tracking the location of the base 16 and the associated manipulator coordinate system MNPL via the manipulator tracker 54B and calculating the pose of the tool 26 based on joint encoder data from the joint encoders 22 (and/or motor encoders) at the joints J1-J6 (using kinematic data) and based on a known geometric relationship between the tool 26 and the manipulator 14. Ultimately, the localizer 44 and the trackers 54A, 54B, 56, 58, PT enable the determination of the pose of the tool 26 and the patient's anatomy so the navigation system 32 knows the relative relationship between the tool 26 and the patient's anatomy. However, in some cases, the manipulator tracker 54B may be out of view of the localizer 44, or the manipulator tracker 54B may not be used. Line-of-sight between one or more of the sensors 50 and the manipulator tracker 54B may be obstructed such that movement of the tool 26 cannot be reliably tracked solely using the manipulator tracker 54B and encoder data. In this case, the tool tracker 54A can be employed to track movement of the tool 26, i.e., the tool tracker 54A is detected by the localizer 44 to determine a pose of the tool 26 (e.g., of the TCP coordinate system of the tool 26).

Referring to FIG. 3, the tool tracker 54A is shown as part of a coupler, such as a sterile coupler 70. The sterile coupler 70 interconnects the manipulator 14 and the tool 26 via mechanical coupling, as described further below. The sterile coupler 70 could interconnect the manipulator 14 and the tool 26 via pneumatic and/or magnetic connections. The sterile coupler 70 has one end mounted to a distal link 18*a* of the manipulator 14 and an opposing end, to which the tool 26 is mounted. In some versions, the sterile coupler 70 is sterilized before use and then removed from its sterile container/packaging before coupling to the distal link 18*a* of the manipulator 14. The sterile coupler 70 may be re-sterilized after use, i.e., the sterile coupler 70 is intended to be at least partially sterile at some point in its life cycle.

In the version shown, the distal link 18*a* includes a first mounting portion, such as a first mounting flange 72 that rotates relative to an adjacent link 18 about axis A6 to define the joint J6 of the manipulator 14. The sterile coupler 70 is mounted to the first mounting flange 72 to rotate with the first mounting flange 72 about the axis A6. The tool 26 has a second mounting portion, such as a second mounting flange 74. The second mounting flange 74 of the tool 26 is mounted to the sterile coupler 70 to rotate with the sterile coupler 70 and the first mounting flange 72 about the axis A6. In some cases, the sterile coupler 70 could be removed and the tool 26 instead mounted directly to the distal link 18*a*. For instance, the second mounting flange 74 is compatible with the sterile coupler 70 and the first mounting flange 72 to selectively make alternative connections. The sterile coupler 70 may be releasably attached to the mounting flanges 72, 74 in any suitable manner, including using snap-fit connections, bayonet-type connections, fasteners, such as bolt, screws, nuts, combinations thereof, etc.

With continued reference to FIG. 3, the tool 26, the sterile coupler 70, the tool tracker 54A, or the tracker body 104 can include a checkpoint CP feature. In FIG. 3, the checkpoint CP is shown in the tool tacker 54A. The checkpoint CP in one implementation is a divot, but other types of geometries (conical, frustoconical) are contemplated. The checkpoint CP is a datum that has a location known/stored to or determinable by the navigation system 32. The location of the checkpoint CP is determinable relative to any component of the system to which the checkpoint CP is rigidly connected (directly or indirectly), i.e., the TCP, the tool 26, the sterile coupler 70, the tool tracker 54, or any part of the manipulator 18. A probe P having a distal tip (e.g., blunt or sharp) is configured to insert the distal tip inserted into the checkpoint CP so that the distal tip bottoms out. The probe P can be like the navigation probe or any probe of any other surgical instrument. The probe P can have a tracker attached to a proximal end thereof. The tracker, e.g., can be the pointer tracker PT when the probe P is the navigation pointer. The navigation system 32 is configured to determine a location of the probe (e.g., based on the pose of the tracker) when the distal tip is inserted into the checkpoint CP and define the location of the checkpoint CP based on the location of the probe. When the checkpoint CP is located on the tool tracker 54A, the navigation system 32 can optionally register the location of the tool tracker 54A to determine the checkpoint location CP. However, the checkpoint CP location can be determined by other means. The navigation system 32 can verify the probe by comparing the checkpoint CP and probe tracker locations to stored calibration data related to the probe. Verification can include determining an identity, size, or installation or the probe P. Additionally, or alternatively, the technique described can be used to verify the location of the tool 26, sterile coupler 70, the tool tracker 54A, or the tracker body 104. This procedure can be performed with any number of tools/probes used during the surgery. For example, one probe can be used to initially determine the checkpoint CP location and a subsequent surgical tool can be verified using the determined checkpoint CP location. By placing the checkpoint CP directly on the tool 26, sterile coupler 70, the tool tracker 54A, or the tracker body 104, the checkpoint CP is directly and quickly accessible to the user who will perform the tool verification steps. Prior verification techniques employ a separate calibration unit that must be brought into the operating room and setup or attached to a patient. Tool verification can now be performed without having to setup any separate units because the checkpoint CP is already located on the tool 26, sterile coupler 70, the tool tracker 54A, or the tracker body 104.

Figure 4B:
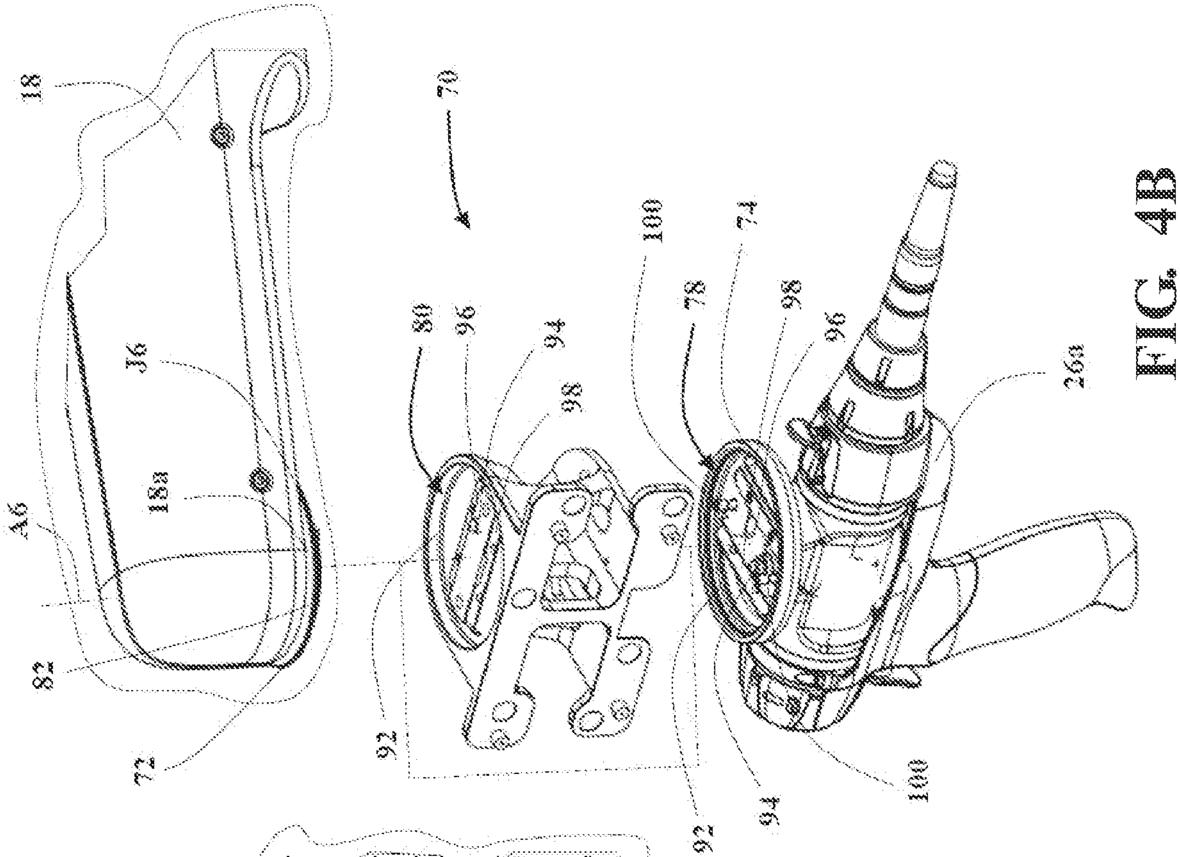
FIGS. 4A and 4B are partially exploded perspective views illustrating connection of the tool to the robotic manipulator via the sterile coupler, according to one implementation.
Figure 4A:
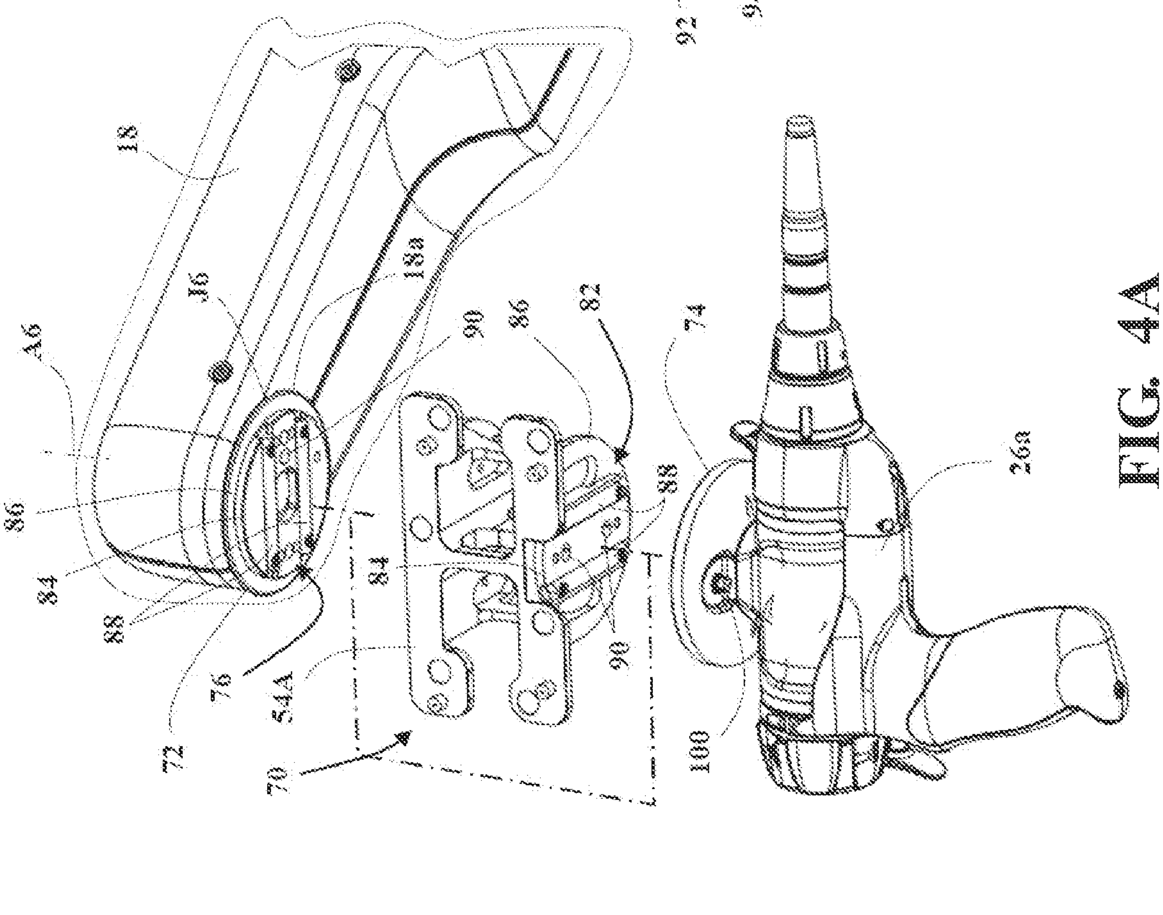
Figure 5B:
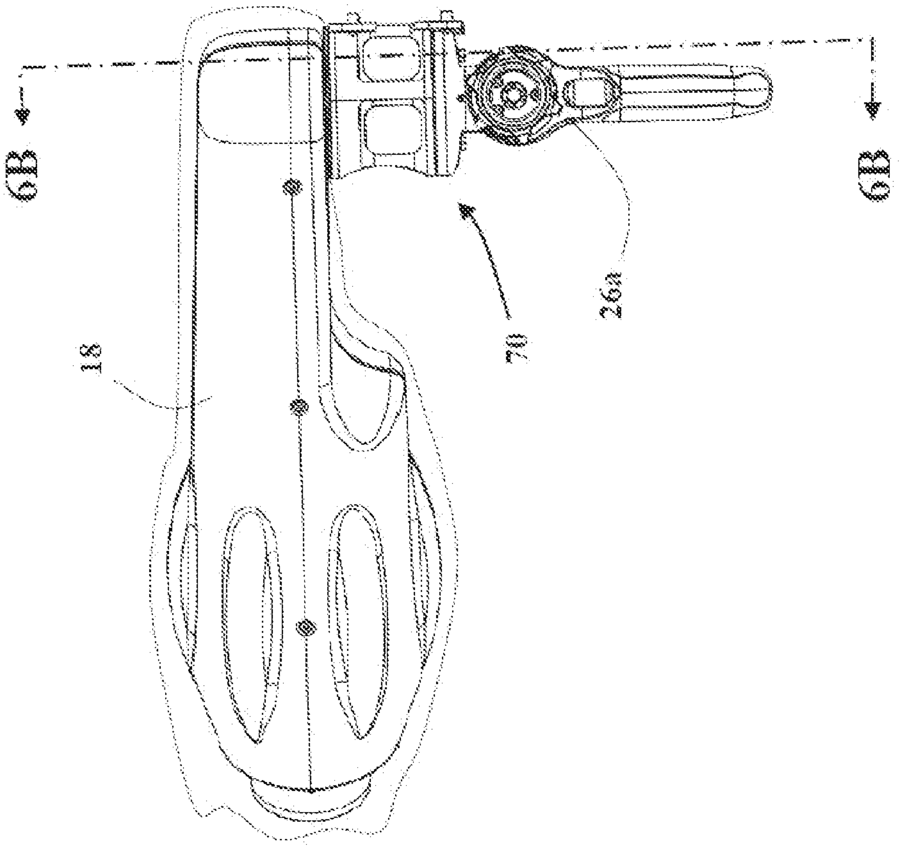
FIGS. 5A and 5B are elevational views of the distal link, sterile coupler, and tool, according to one implementation.
Figure 5A:
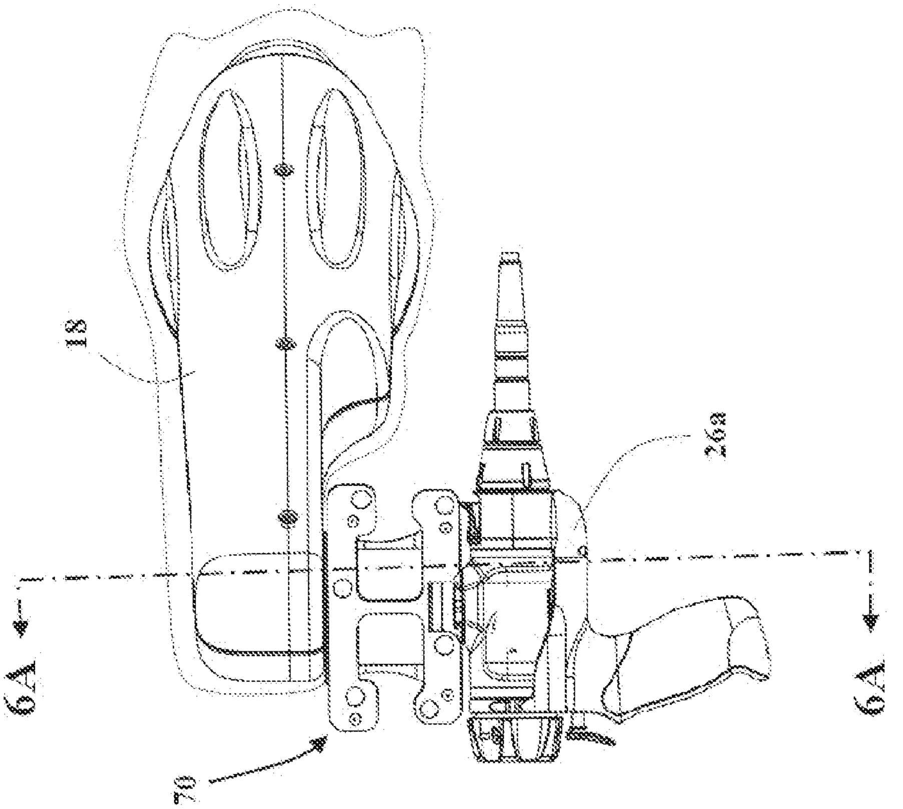

Referring to FIGS. 4A and 4B, example interfaces for making the connections between the tool 26, sterile coupler 70, and the distal link 18*a* of the manipulator 14 are shown. In the version shown, the first mounting flange 72 of the distal link 18*a* includes a first mounting interface 76 (see FIG. 4A) and the second mounting flange 74 of the tool 26 includes a second mounting interface 78 (see FIG. 4B). When directly connecting the second mounting flange 74 to the first mounting flange 72, the second mounting interface 78 directly engages and connects to the first mounting interface 76. The sterile coupler 70 includes a first coupling interface 80 (see FIG. 4B) and a second coupling interface 82 (see FIG. 4A). When indirectly connecting the second mounting flange 74 to the first mounting flange 72 via the sterile coupler 70, the first coupling interface 80 directly engages and connects to the first mounting interface 76 and the second coupling interface 82 directly engages and connects to the second mounting interface 78.

Figure 6A:
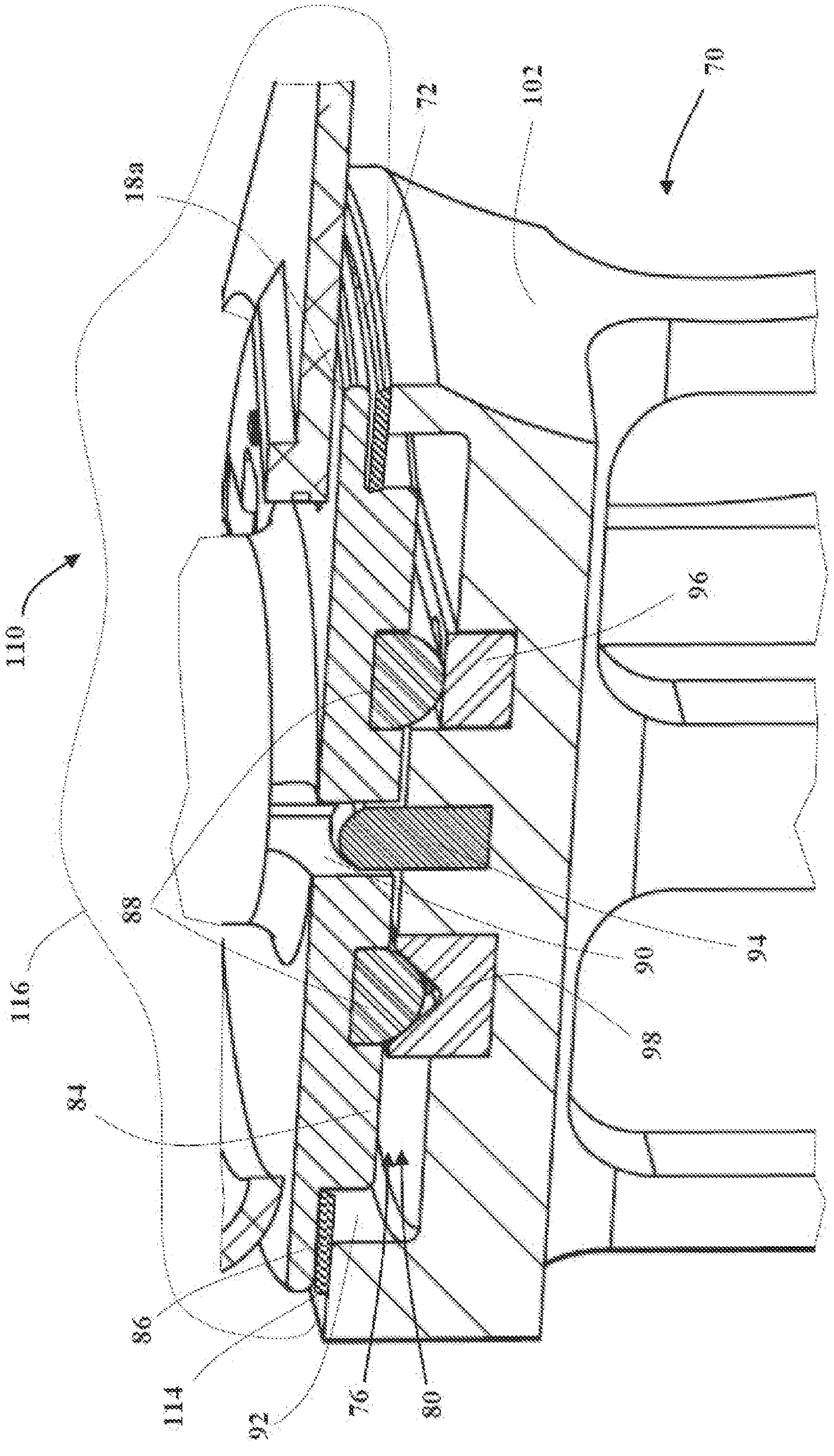
FIG. 6A is a cross-sectional view illustrating a connection between the sterile coupler and the distal link, taken generally along the line 6A-6A in FIG. 5A.

Referring to FIG. 6A, the first mounting interface 76 includes a plurality of first mounting elements. In the version shown, one of the first mounting elements includes a boss 84 (raised portion) that extends from a flange portion 86. The first mounting elements also include two elongate bars 88. Each of the elongate bars 88 has a semi-cylindrically shaped surface that protrudes from a face of the boss 84. The elongate bars 88 may be separate components or integrally formed with the boss 84. In the version shown, the elongate bars 88 are shown as separate components that are fixed to the boss 84 by fasteners. Another first coupling element includes a bore 90 defined through the boss 84.

The first coupling interface 80 includes a plurality of first coupling elements shaped and arranged to align with and/or engage the plurality of first mounting elements of the first mounting interface 76 when connecting the first coupling interface 80 to the first mounting interface 76. In some versions, the first coupling elements include a pocket 92 sized and shaped to receive the boss 84, a pin 94 with a hemi-spherical shaped head sized to fit within the bore 90, a flat block 96 to engage (e.g., by surface contact) one of the semi-cylindrically shaped surfaces, and a V-shaped block 98 to engage (e.g., by surface contact) the other of the semi-cylindrically shaped surfaces. As will be described, other types of kinematic connections are contemplated for the various components.

Figure 6B:
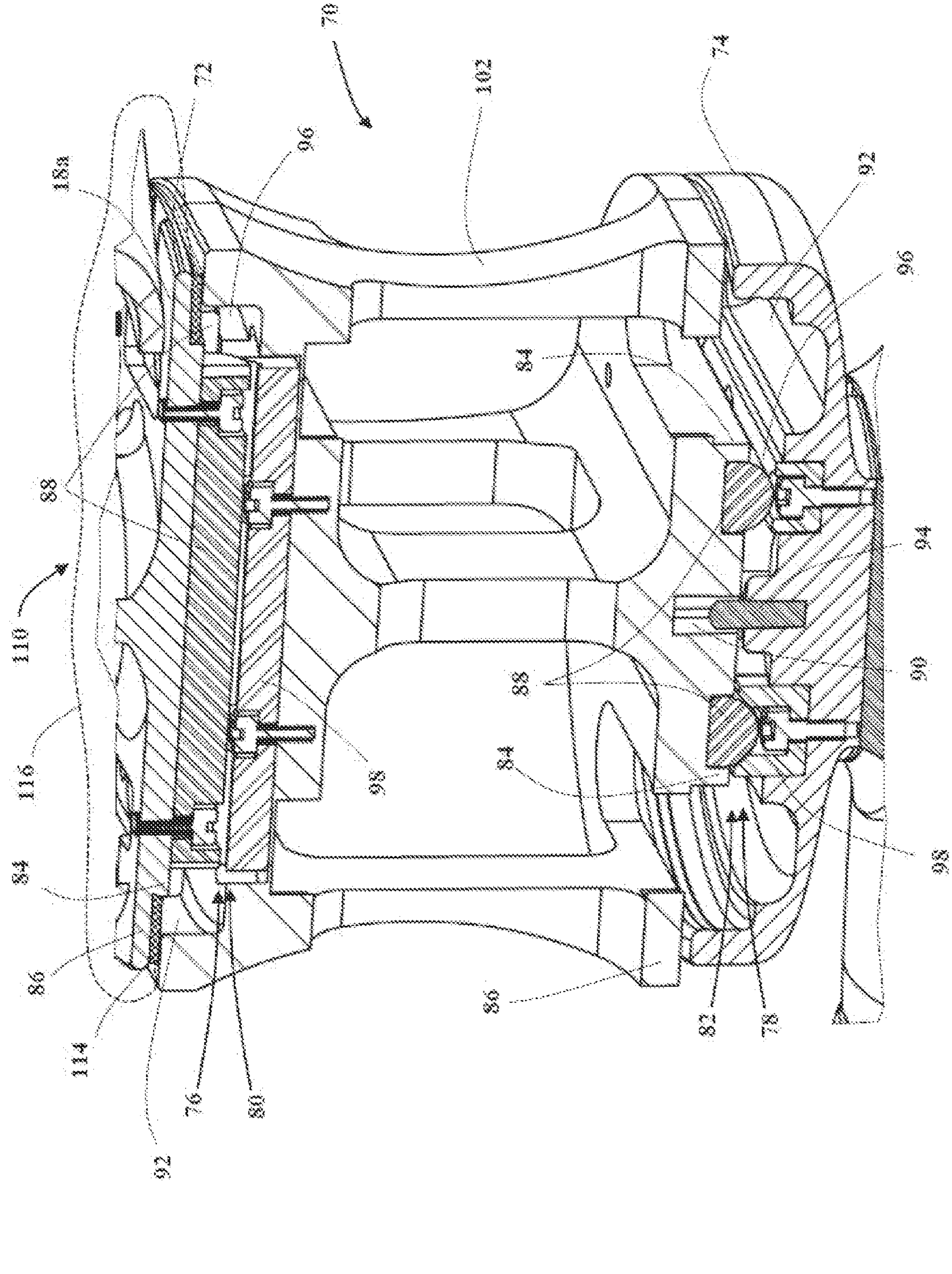
FIG. 6B is a cross-sectional view illustrating a connection between the sterile coupler and the tool, taken generally along the line 6B-6B in FIG. 5B.

Referring to FIG. 6B, the second mounting interface 78 includes a plurality of second mounting elements. In some versions, the second mounting elements are identical in form and function to the first coupling elements and include a pocket 92 sized and shaped to receive the boss 84, a pin 94 with a hemi-spherical shaped head sized to fit within the bore 90, a flat block 96 to engage one of the semi-cylindrically shaped surfaces, and a V-shaped block 98 to engage the other of the semi-cylindrically shaped surfaces.

Figure 8:
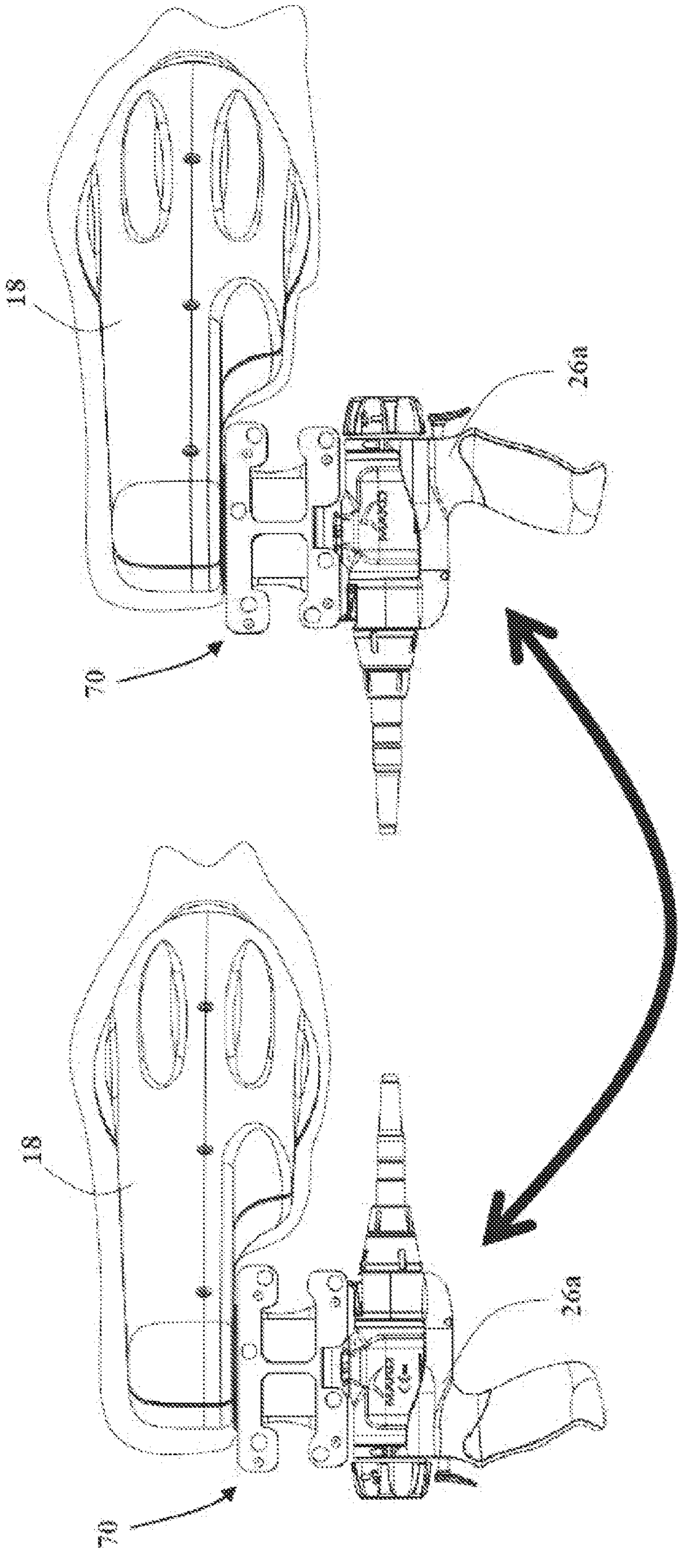
FIG. 8 illustrates how the tool can be attached to the sterile coupler in more than one orientation, according to one implementation.

The second coupling interface 82 includes a plurality of second coupling elements shaped and arranged to align with and/or engage the plurality of second mounting elements of the second mounting interface 78. The second coupling elements may be identical in form and function to the first mounting elements and include a boss 84 that extends from a flange portion 86, two elongate bars 88 with semi-cylindrically shaped surfaces that protrude from a face of the boss 84, and a bore 90 defined through the boss 84. In some versions, there are two bores 90 defined through the boss 84 of the second coupling interface 82 to allow the second mounting interface 78 to be connected to the second coupling interface 82 in two or more orientations, as shown in FIG. 8. In this case, the pin 94 of the second mounting interface 78 can be inserted into either bore 90 such that the second mounting interface 78 is capable of the two different orientations, spaced by 180 degrees, as shown in FIG. 8.

Engagement of the various interfaces 76, 78, 80, 82 and the manner in which the mounting elements and the coupling elements are shaped and arranged for the above-described alignment and/or engagement is best shown in FIGS. 6A and 6B. For instance, FIG. 6A is a partially broken cross-sectional view that illustrates how the elongate bars 88 of the first mounting interface 76 engage (e.g., by surface contact) the flat block 96 and V-shaped block 98 of the first coupling interface 80. The semi-cylindrical nature of the elongate bars 88 is shown wherein one of the semi-cylindrically shaped surfaces engages the flat block 96 (e.g., at a single point in cross-section) and the other semi-cylindrically shaped surface engages the V-shaped block 98 (e.g., at two points in cross-section). As shown in FIG. 6A, the elongate bars 88 of the first mounting interface 76 are parallel to each other. FIG. 6A also shows how the pin 94 fits in the bore 90 to establish the orientation of the sterile coupler 70 with respect to the distal link 18*a*. FIG. 6B is a partially broken cross-sectional view that illustrates how the elongate bars 88 of the second coupling interface 82 engage (e.g., by surface contact) the flat block 96 and V-shaped block 98 of the second mounting interface 78. The semi-cylindrical nature of the elongate bars 88 is shown wherein one of the semi-cylindrically shaped surfaces engages the flat block 96 (e.g., at a single point in cross-section) and the other semi-cylindrically shaped surface engages the V-shaped block 98 (e.g., at two points in cross-section). As shown, the elongate bars 88 of the second coupling interface 82 are parallel to each other and are arranged at 90 degrees with respect to the elongate bars 88 of the first mounting interface 76. FIG. 6B also shows how the pin 94 fits in one of the bores 90 to establish the orientation of the tool 26 with respect to the sterile coupler 70.

When directly connecting the second mounting flange 74 to the first mounting flange 72, the second mounting interface 78 may be secured to the first mounting interface 76 using one or more fasteners, such as machine screws 100. When connecting the sterile coupler 70 to the first mounting flange 72, the first coupling interface 80 may be secured to the first mounting interface 76 using one or more fasteners, such as machine screws. Likewise, when connecting the second mounting flange 74 to the sterile coupler 70, the second mounting interface 78 may be secured to the second coupling interface 82 using one or more fasteners, such as the machine screws 100. When secured together, the mounting elements and coupling elements act to at least semi-kinematically hold the tool 26 to the sterile coupler 70 and to the manipulator 14. In some versions, the mounting elements and coupling elements act to kinematically hold the tool 26 to the sterile coupler 70 and to the manipulator 14 such that exactly six degrees of freedom are constrained between the tool 26 and the sterile coupler 70 and exactly six degrees of freedom are constrained between the sterile coupler 70 and the manipulator 14. In some versions, the mounting elements and the coupling elements act to over constrain the tool 26 to the sterile coupler 70 and to the manipulator 14. In some versions, the mounting elements and coupling elements are formed of rigid materials, such as one or more types of metal, ceramic, combinations thereof, and the like. Other suitable materials and forms of the mounting elements and the coupling elements are also contemplated. Various types of kinematic mounting/coupling elements and associated connections can be used to hold the tool 26 to the sterile coupler 70 and to the manipulator 14. As such, the kinematic mounting/coupling elements are not limited to those shown and described. Such kinematic elements may include, for example, spherical balls, cylinders, semi-spherical elements, semi-cylindrical elements, and the like that are configured to engage, for example, cone-shaped receptacles, V-shaped surfaces, gothic arches, flat surfaces, and the like to constrain, for example, three degrees of freedom, two degrees of freedom, or one degree of freedom depending on the type of surface contact between such elements.

Figure 7B:
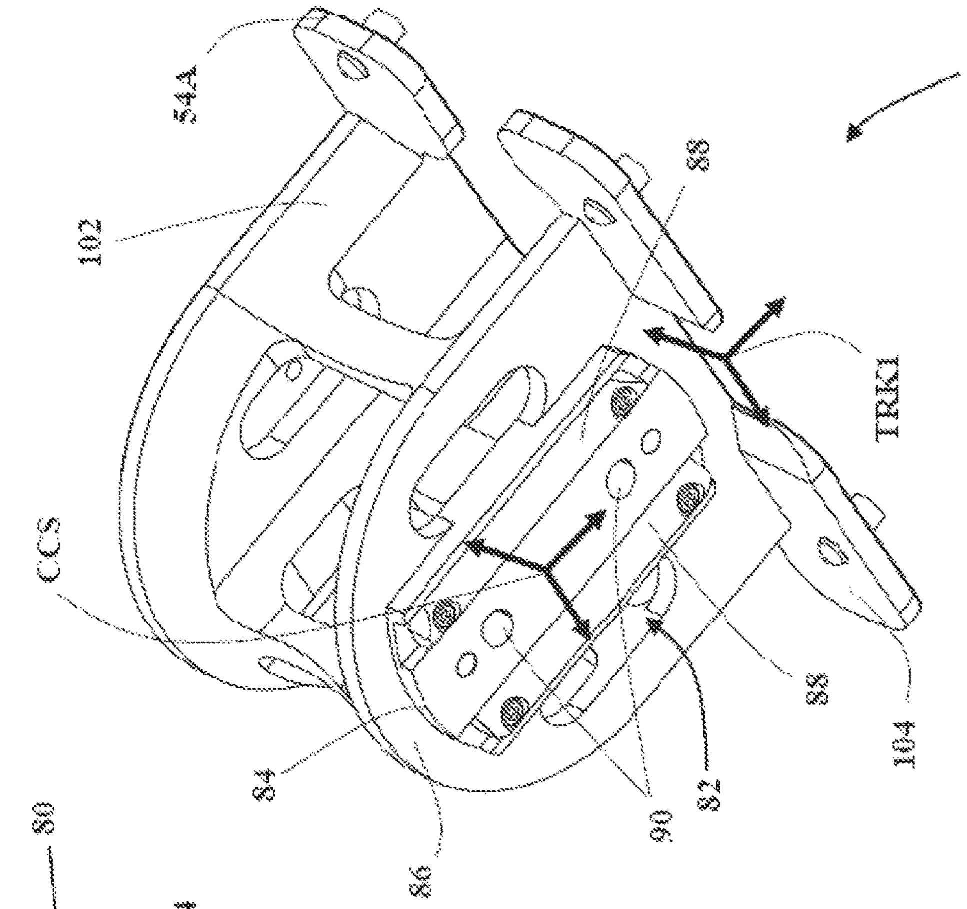
FIGS. 7A and 7B are top and bottom perspective views of the sterile coupler.
Figure 7A:
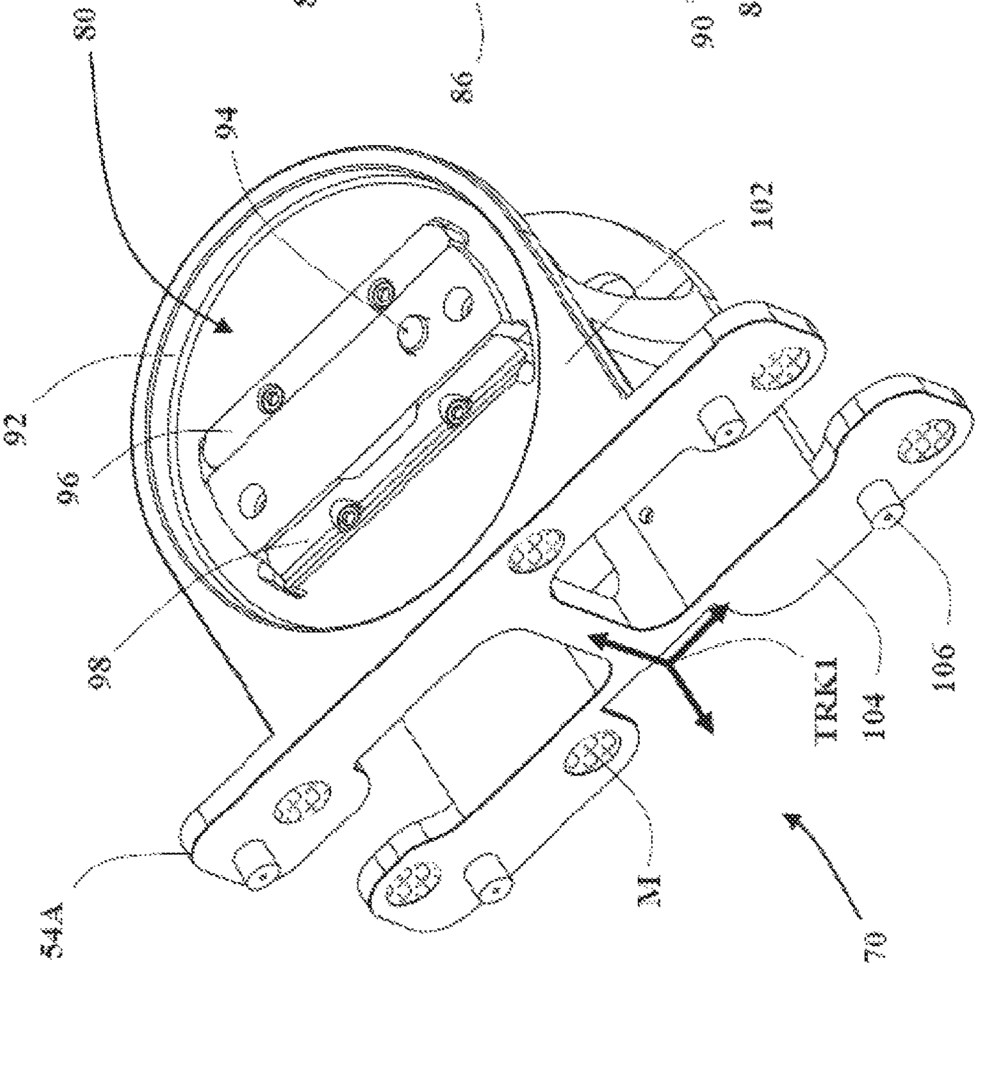

As shown in FIGS. 7A and 7B, the sterile coupler 70 includes a coupler body 102 that may be formed in one-piece or from multiple pieces fixed together. The coupler body 102 has a generally cylindrical shape but may be any suitable shape. The first and second coupling interfaces 80, 82 are located on opposing sides of the coupler body 102 and are integrated with the coupler body 102. Distances between the coupling interfaces 80, 82 can be varied such that a set of sterile couplers 70 provides various spacing options for spacing the tool 26 from the manipulator 14. Accordingly, the sterile coupler 70 may act as a spacer. In some versions, the pin 94, flat block 96, and V-shaped block 98 of the first coupling interface 80 may be integrally formed with the coupler body 102 or may be separate parts fixed to the coupler body 102 by fasteners, welding, adhesive, or the like. Similarly, the boss 84, two elongate bars 88, and bores 90 may be integrally formed with the coupler body 102 or may be separate parts fixed to the coupler body 102 by fasteners, welding, adhesive, or the like.

The tool tracker 54A has a tracker body 104 for supporting the tracking elements/markers M (e.g., passive or active). In the version shown in FIGS. 7A and 7B, the tracker body 104 is integrally formed with the coupler body 102 and supports six tracking elements/markers M. Alternatively, the tracker body 104 may be releasably attached to the coupler body 102. In other examples, one or more tracker parts can be releasably attached to the tracker body 104. For example, the tracker parts can include a reflective material layer to interact with tracking signals and a cover that is disposed over the reflective material layer so that when the tracker parts are assembled to the tracker body 104, the reflective material can be captured between the tracker body 104 and the cover. Projections 106 may also extend from a front surface of the tracker body 104 to provide pronounced features for measurement via a coordinate measuring machine (CMM). Four projections are shown, but any suitable number of projections may be provided as touch points for the CMM when determining the relationship of a tracker coordinate system TRK1 of the tool tracker 54A to other coordinate systems, such as a coupler body coordinate system CCS associated with the coupler body 102. The coupler body coordinate system CCS can additionally or alternatively be associated with the second mounting flange 74 of the tool 26, e.g., when the tool 26 is coupled to the coupler body 102.

Figure 9B:
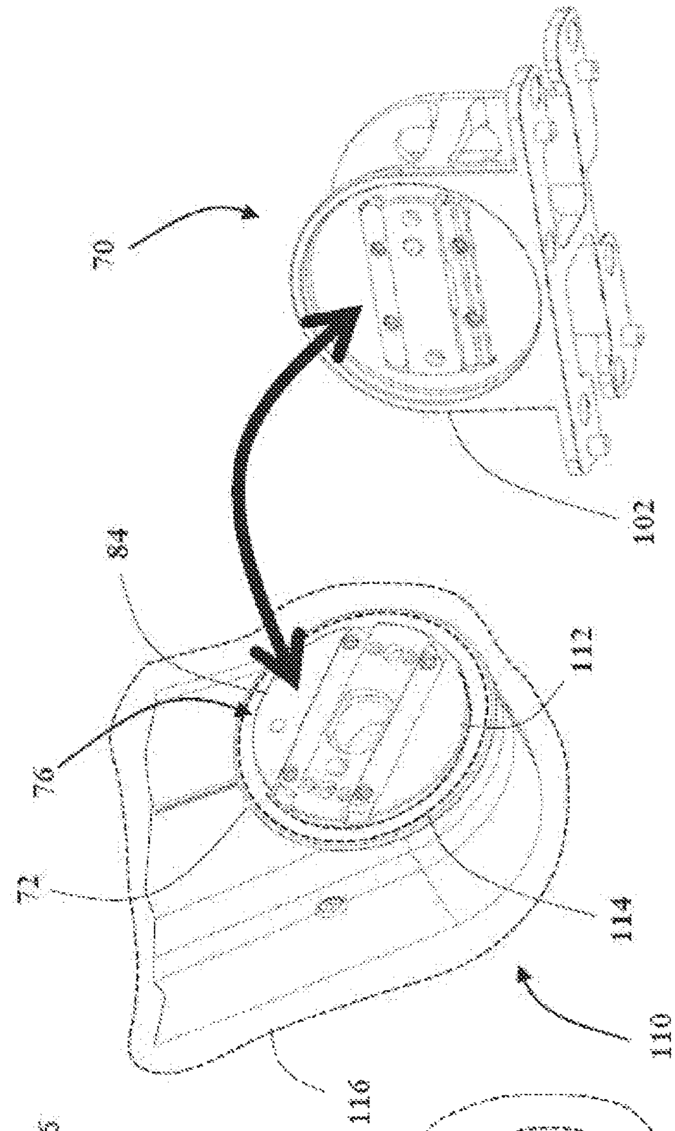
FIGS. 9A and 9B illustrate attachment of a sterile drape to the distal link and attachment of the sterile coupler over the sterile drape, according to one implementation.
Figure 9A:
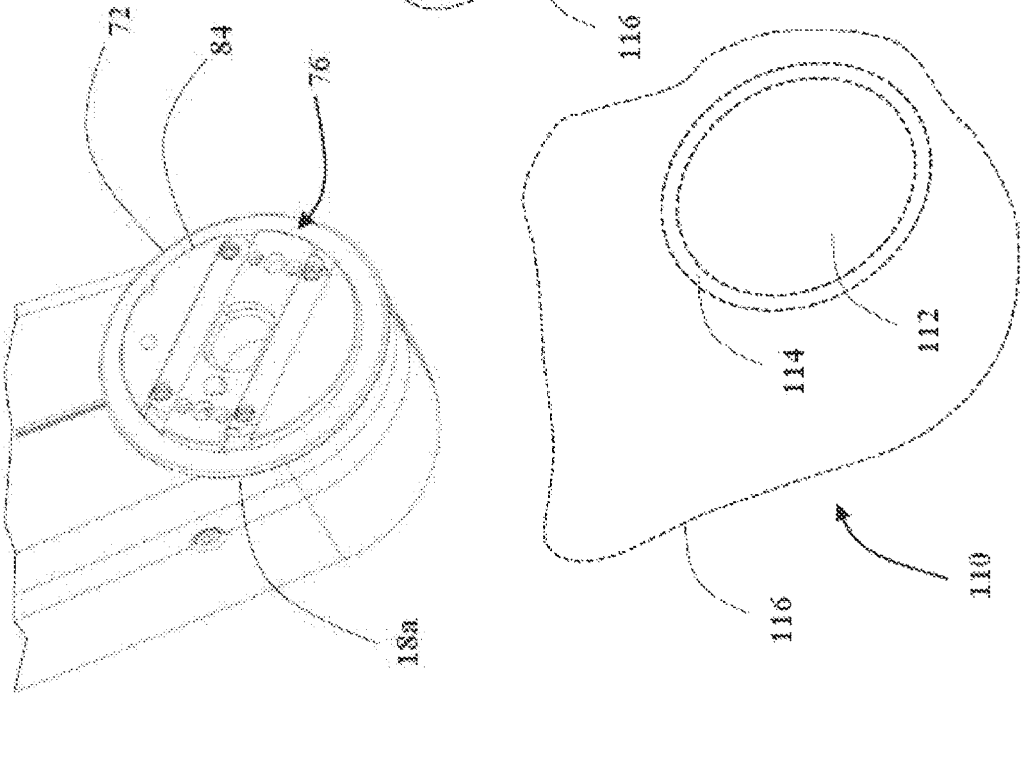

A drape, such as a sterile drape 110, is partially shown in FIG. 9A for fitting over the distal link 18*a* and is shaped to be disposed over the manipulator 14 (see FIG. 1). The sterile drape 110 has an opening 112 adapted to be disposed about the first mounting interface 76. The sterile drape 110 may have a ring 114 that at least partially defines the opening 112 and a more flaccid, covering portion 116 that extends from the ring 114 to be disposed over the manipulator 14. The sterile drape 110 has an interior surface and an exterior surface. The interior surface is placed adjacent to the manipulator 14 during surgery. In the example shown in FIG. 1, the sterile drape 110 is fitted to the manipulator 14 to generally encompass the manipulator 14 and the cart 20. The sterile drape 110 is provided to maintain sterility of the surgical site and the tool 26 during the surgical procedure by creating a sterile field barrier between the tool 26 and the robotic manipulator 14 so that, for instance, a different tool 26 (e.g., burr, saw, drill, screwdriver, impactor, endoscope, etc.) could be attached to the manipulator 14 without requiring re-draping of the manipulator 14, i.e., the sterile field would be sufficiently maintained.

The ring 114 and covering portion 116 may be formed of polyethylene, polyurethane, polycarbonate, combinations thereof, and/or any other suitable materials. The covering portion 116 may be attached to the ring 114 by ultrasonic welding, tape, adhesive, or the like, or the covering portion 116 may be integrally formed with the ring 114. The covering portion 116 is attached to the ring 114 so that no perforations are present other than the opening 112, i.e., the drape forms a continuous barrier with the ring 114. In some versions, the ring 114 is formed to be more rigid than the covering portion 116, which is relatively more flexible to drape over the manipulator 14. In some versions, the sterile drape 110 may be connected to the coupler 70 or form part of the coupler 70. For example, as shown in FIG. 6A, instead of the ring 114 floating between the flange 86 and the coupler 70 as shown (or it could be attached to the flange 86 via adhesive, tape, magnets, or other fasteners), the ring 114 may be connectable to the coupler body 102 in the same location shown via adhesive, tape, magnets, or other fasteners, and would thus be connected to the coupler 70.

The sterile coupler 70 cooperates with the sterile drape 110 to create the sterile field barrier. In some versions, the manipulator 14 and its first mounting flange 72 are considered non-sterile, but the tool 26 is considered sterile. The manipulator 14 and its first mounting flange 72 are covered by a combination of the sterile drape 110 and the sterile coupler 70 to create the sterile field barrier/boundary between the tool 26 and the manipulator 14, e.g., the sterile drape 110 covers a majority of the manipulator 14 and the sterile coupler 70 covers the first mounting interface 76 of the first mounting flange 72. The sterile coupler 70 may partially or fully cover the first mounting interface 76.

Like the sterile coupler 70, the sterile drape 110 may be sterilized before use, removed from its sterile container/packaging, and then placed on the manipulator 14. Typically, the sterile drape 110 is discarded after a single use but may be reusable and re-sterilized after each use. The sterile drape 110 is intended to be at least partially sterile at some point in its life cycle. The sterile coupler 70 may be reusable or may be intended for single use and disposable. When the sterile drape 110 is integrated into the sterile coupler 70, the entire assembly may be disposable. Furthermore, in configurations where the tracker body 104 is releasably attachable to the coupler body 102, or the one or more tracker parts (e.g., reflective material layer and cover) are releasably attached to the tracker body 104, the tracker body 104 and/or tracker parts may be reusable or may be intended for single use and disposable.

As surgical personnel begin preparations for a surgical procedure, the sterile drape 110 is first fitted over the distal link 18*a* by placing the ring 114 about the first mounting interface 76 and onto the first mounting flange 72. More specifically, the ring 114 is fitted over the boss 84 of the first mounting interface 76 so that the boss 84 protrudes through the opening 112 (see FIG. 9B). One or more links 18 of the manipulator 14 are then covered with the covering portion 116 (see FIG. 1). The cart 20 may also be at least partially covered by the covering portion 116. The sterile coupler 70 is then fastened to the first mounting flange 72 via fasteners or the like with the ring 114 captured between the coupler body 102 and the first mounting flange 72 (see also FIG. 6A). The interfaces 76, 78, 80, 82 are configured to facilitate releasable attachment of the sterile coupler 70 to the first mounting flange 72, as well as releasable attachment of the second mounting flange 74 to the sterile coupler 70. The second mounting flange 74 can be released from the sterile coupler 70 without disrupting the sterile field barrier created by the sterile coupler 70 and the sterile drape 110.

Figure 10A:
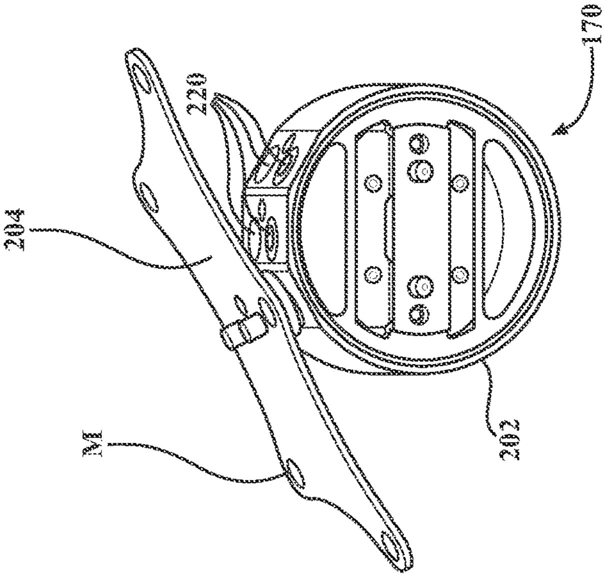
FIGS. 10A, 10B, and 10C illustrate how a tracker can be attached to a coupler body of a sterile coupler in more than one orientation, according to one implementation.
Figure 10B:
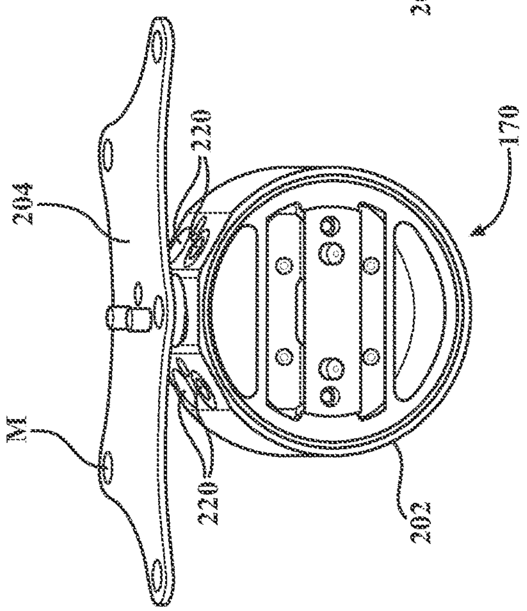
Figure 10C:
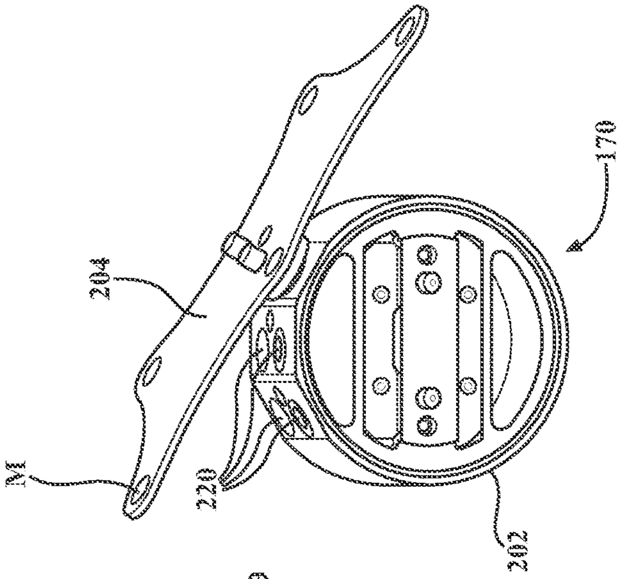

An alternative sterile coupler 170 is shown in FIGS. 10A through 10C. In this version, the sterile coupler 170 has the same features as the sterile coupler 70, except that the tracker body 204 is separate from the coupler body 202 and is connectable to the coupler body 202 in at least two different orientations, such as the three different orientations shown. The tracker body 204 may be connectable via one or more fasteners, or the like. The tracker body 204 can thus be oriented in a manner that provides the best line-of-sight for the tracking elements/markers M to the sensors 50 of the localizer 44. As shown, the coupler body 202 has a plurality of mounting locations 220 at which the fasteners can attach the tracker body 204. The mounting locations 220, for example, may include threaded bores, and the fasteners could be machine screws, or other type of threaded fastener to connect the tracker body 204 to the coupler body 202 at one or more of the mounting locations 220. Alternative mounting arrangements for the tracker body 204 are also contemplated.

Figure 11A:
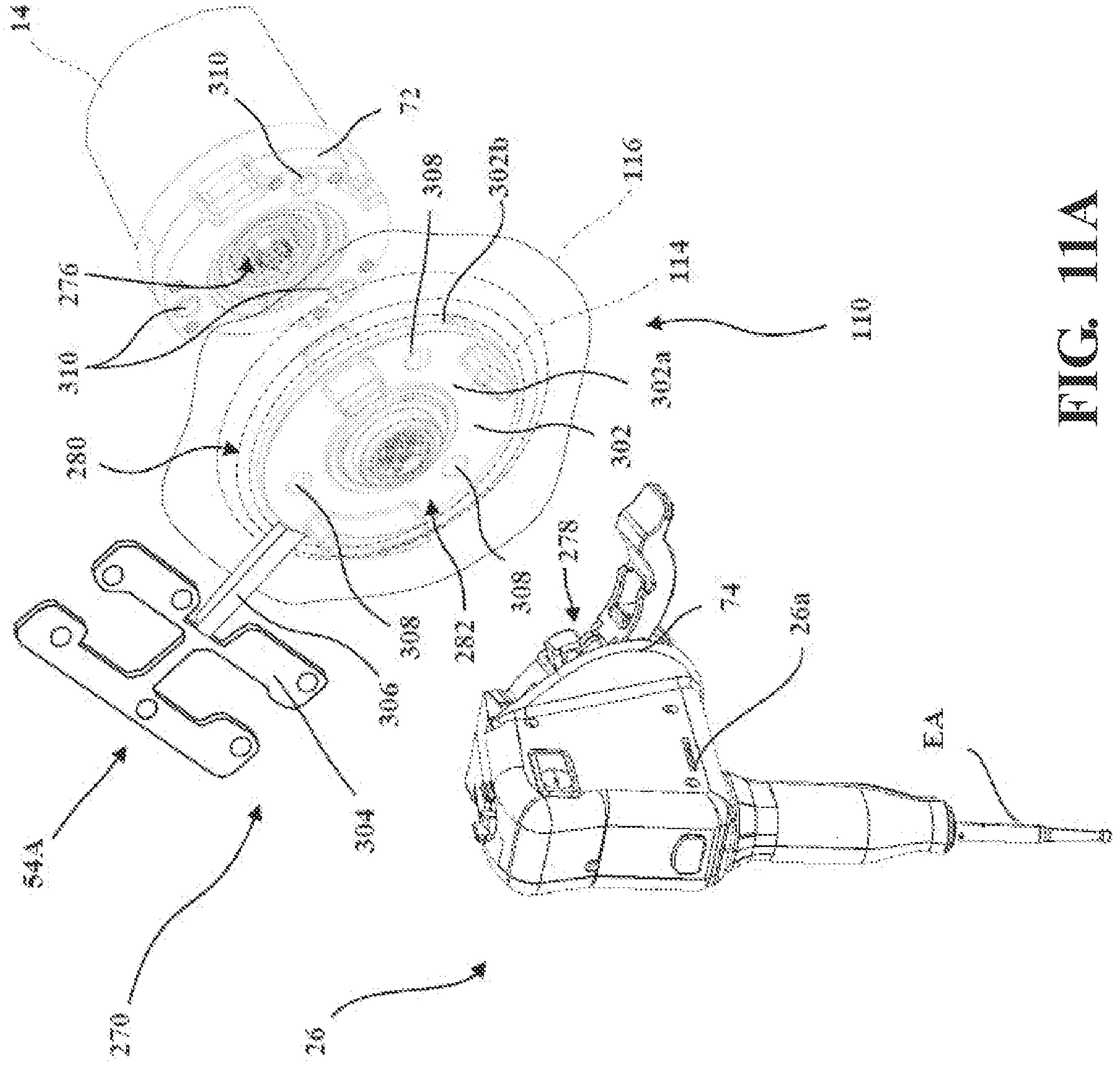
FIGS. 11A and 11B are partially exploded, perspective views showing an alternative sterile coupler, according to one implementation.
Figure 11B:
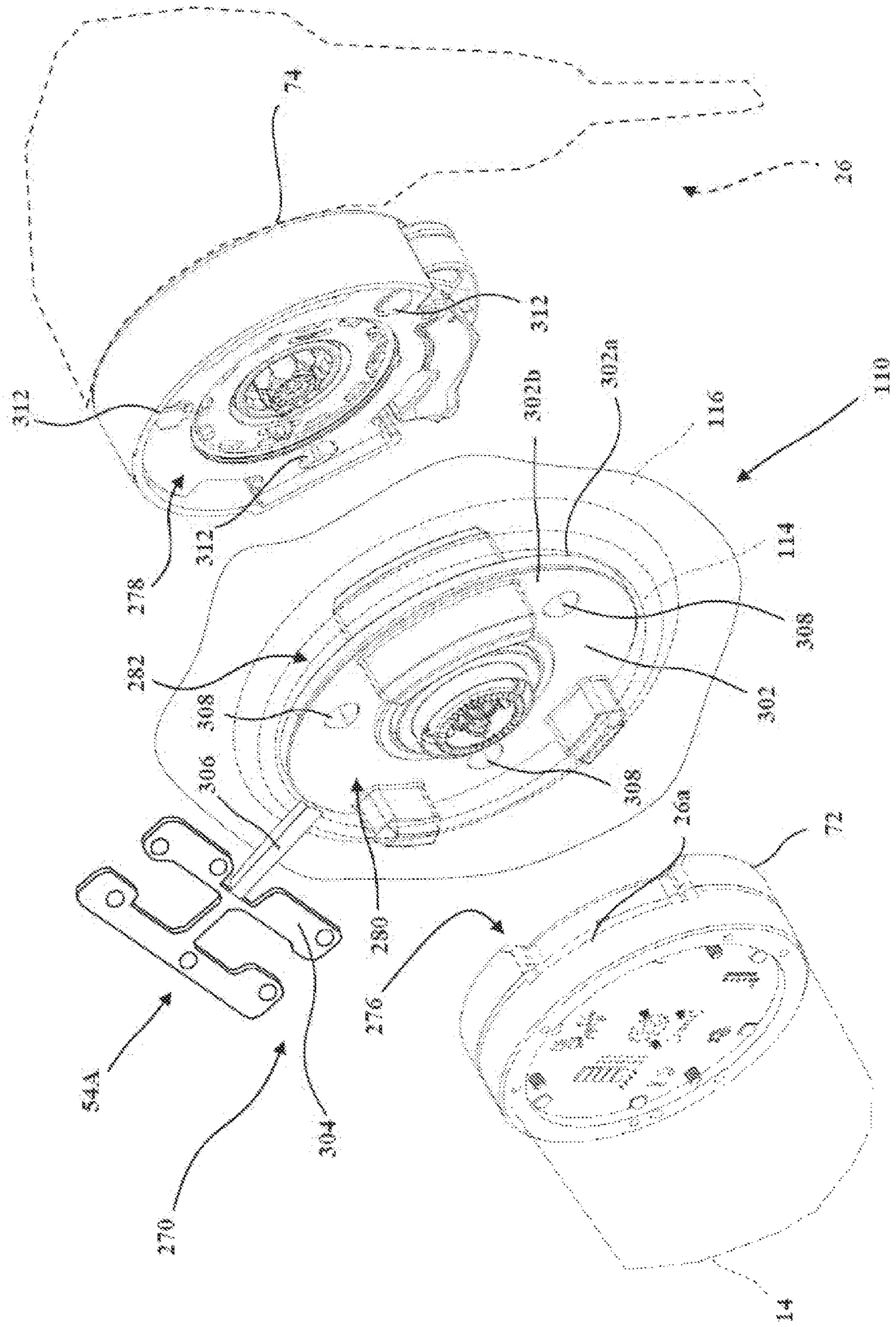

Another alternative sterile coupler 270 is shown in FIGS. 11A and 11B for interconnecting the manipulator 14 and the tool 26. In this version, the first mounting flange 72 and the second mounting flange 74 have different forms from those previously shown. The coupler body 302 includes first and second interface plates 302*a*, 302*b*, connected together, that provide the first and second coupling interfaces 280, 282 that engage and connect to the first and second mounting interfaces 276, 278. In some versions, there is only a single interface plate and/or a one-piece coupler body. In the version shown, the first and second coupling interfaces 280, 282 rely on a plurality of coupling elements in the form of kinematic coupling elements, such as spherical balls 308 (three balls are shown) to engage the first and second mounting interfaces 276, 278. One side of the balls 308 engages the first mounting interface 276, while the other side of the balls 308 engages the second mounting interface 278. The balls 308 are sized and shaped to engage corresponding kinematic mounting elements of the first and second mounting interfaces 276, 278, such as receptacles 310, 312, which may be cone-shaped receptacles, V-shaped receptacles, flats, and/or combinations thereof. In some versions, the balls 308 are sized and shaped to engage the corresponding kinematic mounting elements to constrain exactly six degrees of freedom between the tool 26 and the sterile coupler 270 and/or between the sterile coupler 270 and the manipulator 14. The tool 26, sterile coupler 270, and manipulator 14 can be secured together via clamps, fasteners, and the like to hold the kinematic coupling elements and kinematic mounting elements in engagement. Examples of the first and second interface plates 302*a*, 302*b*, and the first and second mounting interfaces 276, 278 are shown in U.S. Patent Application Publication No. 2020/0170724, entitled, "Mounting System With Sterile Barrier Assembly For Use In Coupling Surgical Components," filed on Dec. 4, 2019, which is hereby incorporated herein by reference in its entirety and U.S. Patent Application Publication No. 2016/0242861, entitled, "Sterile Barrier Assembly, Mounting System, And Method For Coupling Surgical Components," filed on Feb. 19, 2016, which is hereby incorporated herein by reference in its entirety.

In this version, the sterile drape 110 may be operatively attached to the sterile coupler 270 and may be secured between the first and second interface plates 302*a*, 302*b*, or the sterile drape 110 may be attached to one of the interface plates, e.g. on a side or an outer surface thereof. An alternative ring 114 of the sterile drape 110 may be releasably attached to the sterile coupler 270 prior to the surgical procedure. One example of the alternative ring 114 is shown and described in U.S. Patent Application Publication No. 2019/0099232, entitled "Sterile Drape Assembly For Surgical Robot," filed on Oct. 4, 2018, which is hereby incorporated herein by reference in its entirety. The tool tracker 54A for the sterile coupler 270 is mounted and fixed to an arm 306. The tracker body 304 of the tool tracker 54A may also be integrally formed with the arm 306. The arm 306 is fixed to and extends from the coupler body 302 (e.g., from one or both the interface plates 302*a*, 302*b*). The arm 306 may be integrally formed with the coupler body 302 (e.g., with one or both the interface plates 302*a*, 302*b*).

Due to the integration of the tool tracker 54A into the sterile coupler 70, 170, 270 tracking of the tool 26 relative to the patient's anatomy may rely on certain relationships between various coordinate systems of the system 10. A localization engine 400 is a software module that can be considered part of the navigation system 32 and is employed to assist with establishing such relationships (see FIG. 2). Components of the localization engine 400 run on navigation controller 36. In some embodiments, the localization engine 400 may run on the manipulator controller 24.

Prior to the start of the surgical procedure, additional data are loaded into the navigation controller 36, such as calibration and/or registration data. Based on the pose of the trackers 54A, 54B, 56, 58, PT determined by the localizer 44 in the localizer coordinate system LCLZ, and the additional data, navigation controller 36 ultimately determines, in a common coordinate system, the pose of the TCP of the tool 26 relative to the tissue against which the tool 26 is to be applied at the surgical site. The navigation controller 36 also generates image signals that indicate the relative pose of the tool 26 to the tissue. These image signals are applied to the displays 38. Displays 38, based on these signals, generate images that allow the surgeon and staff to view the relative position of the tool 26 to the surgical site.

The additional data may include calibration data or registration data, such as spatial and/or transformation data relating poses of coordinate systems of the trackers 54A, 54B, 56, 58 to coordinate systems of: the tool 26; the first mounting flange 72; the base 16; one or more of the links 18; the patient's anatomy; 3-D anatomy models; or the like. This data may be determined pre-operatively or intra-operatively. Such data can be determined by measurement, e.g., using a coordinate measuring machine (CMM), navigation probe and divot, registration/calibration, and the like. In some embodiments, navigation controller 36 forwards these data to the manipulator controller 24. The manipulator controller 24 can then use the data to control the manipulator 14 as described in U.S. Pat. No. 8,010,180 or 9,566,122, both of which are incorporated by reference herein.

Coordinate transformer 402 is a navigation system software module that runs on navigation controller 36. During the surgical procedure, the coordinate transformer 402 receives the localizer data and the additional data (e.g., the registration/calibration data). Based on these data, the previously loaded data, and the encoder data from the manipulator 14, the coordinate transformer 402 generates data indicating the relative poses of the TCP relative to the anatomy of interest. Coordinate transformer 402 is also operable to determine the pose of any coordinate system described herein relative to another coordinate system by utilizing known transformation techniques, e.g., translation and rotation of one coordinate system to another based on the various transforms described herein. As is known, the relationship between two coordinate systems is represented by a six degree of freedom relative pose, a translation followed by a rotation, e.g., the pose of a first coordinate system in a second coordinate system is given by the translation from the second coordinate system's origin to the first coordinate system's origin and the rotation of the first coordinate system's coordinate axes in the second coordinate system. The translation is given as a vector. The rotation is given by a rotation matrix.

Figure 12:
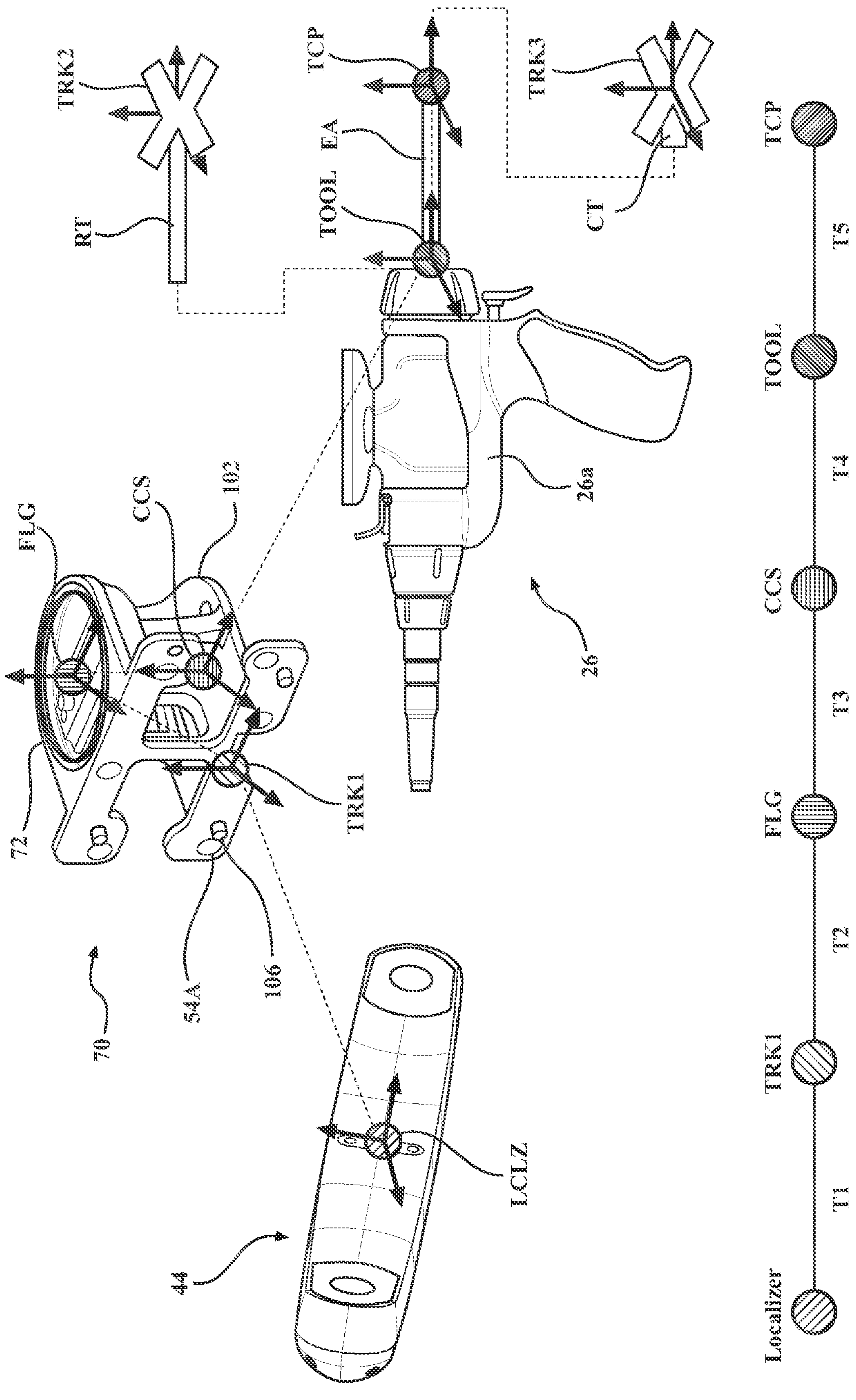
FIG. 12 illustrates a chain of transforms associated with tracking a pose of the tool, according to one implementation.
Figure 13:
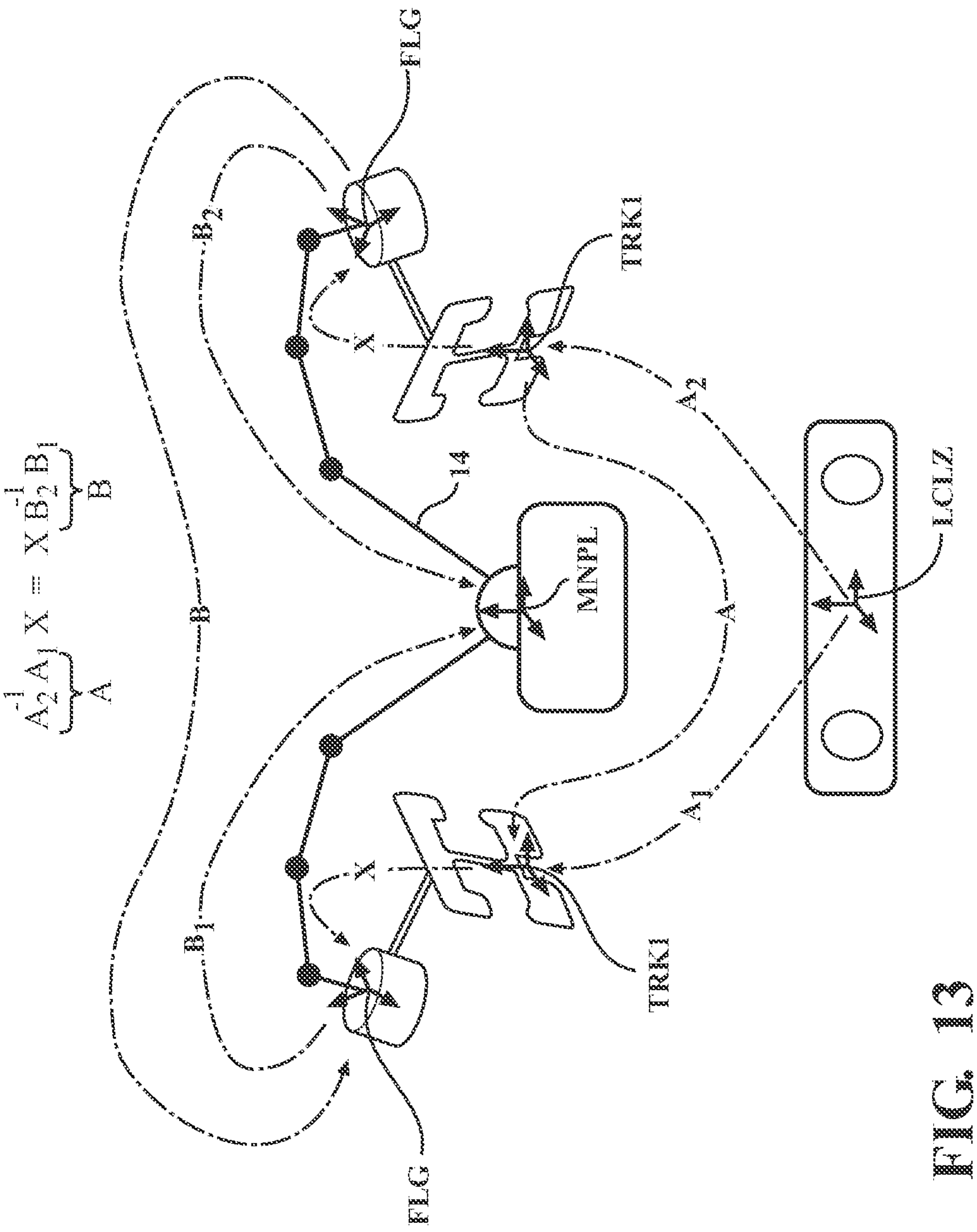
FIG. 13 illustrates a method of determining a transform from the tracker to the sterile coupler used in the chain of transforms from FIG. 12, according to one implementation.
Figure 16:
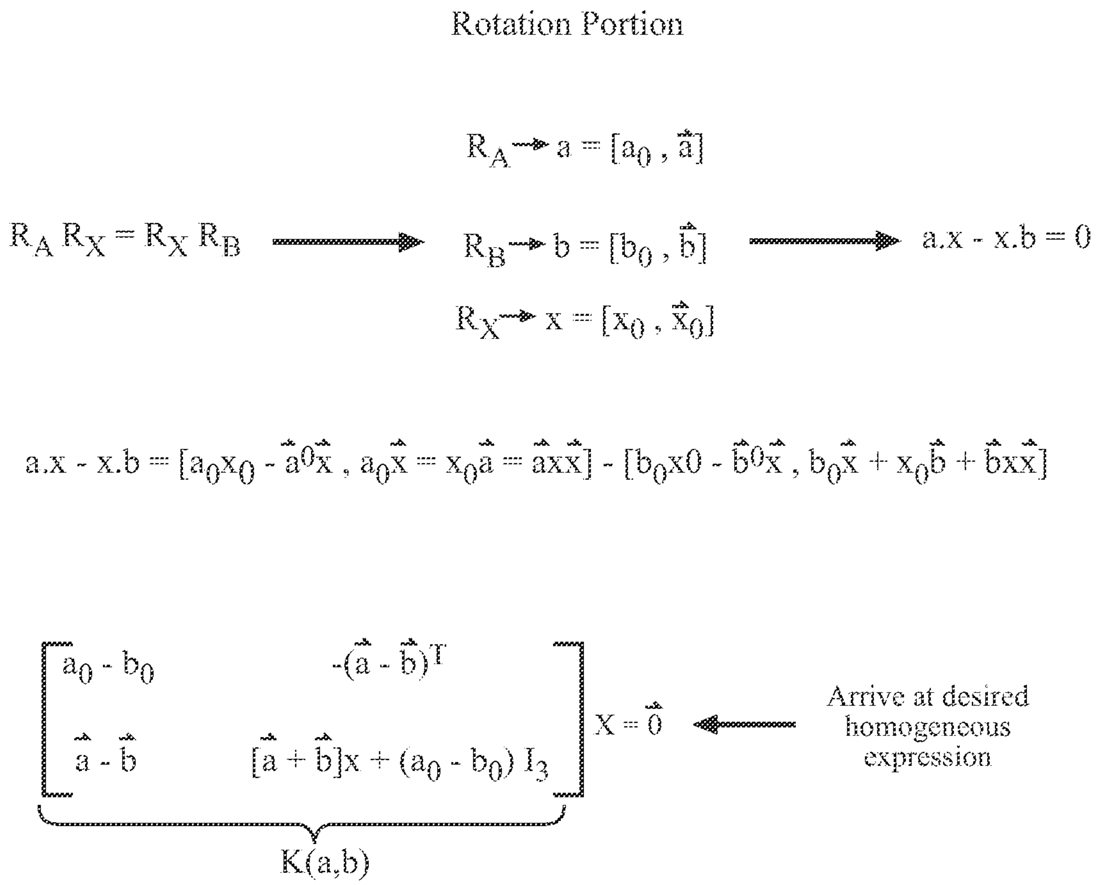

In some examples, the navigation system 32 determines the pose of the TCP coordinate system in the localizer coordinate system LCLZ via the transforms T1-T5 shown in FIG. 12. The first transform T1 can be determined based on localizer data that indicates a pose of the tracker coordinate system TRK1 of the tool tracker 54A in the localizer coordinate system LCLZ. The second transform T2 can be determined based on calibration/registration data that maps the pose of a flange coordinate system FLG of the first mounting flange 72 relative to the tracker coordinate system TRK1. A registration process can be employed to determine the second transform T2, as described further below. Additionally, or alternatively, projections 106 may be formed on the tool tracker 54A to find the second transform T2. In this case, the sterile coupler 70 is first connected to a first fixture (not shown) representative of the first mounting flange 72 and MINI measurements are made on the projections 106 and the first fixture with respect to the first fixture's coordinate system. The locations of the projections 106 relative to the tracker coordinate system TRK1 are known and stored in memory in the navigation system 32.

The relationship between the flange coordinate system FLG and the coupler coordinate system CCS is determined to yield the third transform T3. This may be determined by connecting the sterile coupler 70 to the first fixture representing the first mounting flange 72 and connecting a second fixture to the sterile coupler 70 at the second coupling interface 82. Measurements are then made of points on the second fixture. This CMM data is then point paired with another CMM data set of the same points when the second fixture is directly coupled to the first fixture (e.g., without the sterile coupler 70).

The fourth transform T4 may be determined by attaching a registration tool RT with a separate tracker to the tool driver 26*a*, wherein a coordinate system of the registration tool RT (e.g., of its separate tracker TRK2) has a known, geometric relationship to the tool coordinate system TOOL when the registration tool RT is attached to the tool driver 26*a*. Accordingly, the localizer 44 can determine the pose of the separate tracker having tracker coordinate system TRK2 in the localizer coordinate system LCLZ and thereafter, based on the known relationship of the separate tracker TRK2 to the tool coordinate system TOOL, and having already determined the transforms T1-T3, the navigation system 32 can determine the fourth transform T4. Additionally, or alternatively, the fourth transform T4 can be determined based on constant geometric values associated with each tool 26 that are extracted from prior CMM measurements.

The fifth transform T5 can similarly be determined with a calibration tool CT with a separate tracker having tracker coordinate system TRK3 by placing the calibration tool CT (or the navigation probe) at a known location relative to the localizer coordinate system LCLZ (e.g., in a divot on the energy applicator EA having a known, geometric relationship to the TCP coordinate system), such that the navigation system 32 can thereafter determine the fifth transform T5, having already determined the transforms T1-T4. Additionally, or alternatively, the energy applicators can be manufactured with strict tolerances so that the relationship between the tool driver 26*a* and the TCP and the associated fifth transform T5 is already known and stored in memory. In some cases, the additional calibration step can be used to verify this known data, e.g., to ensure that the energy applicator wasn't bent or otherwise damaged. During operation, these transforms and/or other transforms can be determined using more than one technique. For instance, the position of the TCP can be determined using a set of transforms that rely heavily on encoder-based data and separately determined using a set of transforms that rely heavily on navigation-based data. These values can then be compared to detect errors in the system 10. Such error detection methods are described, for example, in U.S. Pat. No. 10,660,715, entitled "Techniques For Detecting Errors Or Loss Of Accuracy In A Surgical Robotic System," filed on Dec. 13, 2017, hereby incorporated herein by reference.

Referring to FIGS. 13 through 18, example steps are shown for a hand-eye registration algorithm employed by the coordinate transformer 402 to automatically determine the second transform T2 previously mentioned. In this case, referring first to FIG. 13, the manipulator 14 is moved so that the first mounting flange 72 represented by the flange coordinate system FLG, the sterile coupler 70, 170, 270 represented by the coupler coordinate system CCS, and the tool tracker 54A represented by the tracker coordinate system TRK1 are all moved to two different poses at times t1 and t2. As a result of this movement, two different paths for calculating transforms are created. One path starts with the transform A1 from the localizer coordinate system LCLZ to the tracker coordinate system TRK1, continues with the transform x from the tracker coordinate system TRK1 to the flange coordinate system FLG (transform x is the same as transform T2 previously described), and then ends with the transform B1 from the flange coordinate system FLG to the manipulator coordinate system MNPL. The other path starts with the transform A2 from the localizer coordinate system LCLZ to the tracker coordinate system TRK1, continues with the transform x from the tracker coordinate system TRK1 to the flange coordinate system FLG (transform x is the same as transform T2 previously described), and then ends with the transform B2 from the flange coordinate system FLG to the manipulator coordinate system MNPL. The transforms A1, A2 are known from the localizer data and the transforms B1, B2 are known from encoder data of the manipulator 14. Transform A, as shown, can be calculated from the known transforms A1, A2 and transform B, as shown, can be calculated from the known transforms B1, B2. Using the relationships shown in FIG. 13, the algorithm can be simplified to Ax=xB, which equates two transforms. The transform x can be solved by calculating rotation and translation separately, as outlined in FIGS. 13 through 17.

Several embodiments have been described in the foregoing description. However, the embodiments discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described.

The invention claimed is:

1. A robotic surgical system for use with a localizer, the robotic surgical system comprising:
- a robotic manipulator including a plurality of links and a plurality of joints, wherein one of the plurality of links is a distal link that includes a first mounting interface having a plurality of first mounting elements;
- a drape shaped to be disposed over the robotic manipulator;
- a cutting tool including a second mounting interface having a plurality of second mounting elements; and
- a coupler configured to cooperate with the drape to create a sterile field barrier between the cutting tool and the robotic manipulator, the coupler including:
- a coupler body, including:
  - a first side presenting a first coupling interface being directly connectable to the first mounting interface of the distal link, the first coupling interface including a plurality of first coupling elements arranged to align with and engage the plurality of first mounting elements to facilitate direct connection between the first side of the coupler body and the distal link;
  - a second side opposite to the first side, the second side presenting a second coupling interface being directly connectable to the second mounting interface of the cutting tool, the second coupling interface including a plurality of second coupling elements arranged to align with and engage the plurality of second mounting elements to facilitate direct connection between the second side of the coupler body and the cutting tool;
  - mounting features formed on the coupler body at a location between the first side and the second side; and
  - a tracker supporting tracking elements and comprising attachment features configured to releasably attach to the mounting features of the coupler body, the tracker configured to be detected by the localizer to determine a pose of the cutting tool.

2. The robotic surgical system of claim 1, wherein the second mounting interface is connectable to the second coupling interface in at least two different orientations.

3. The robotic surgical system of claim 1, wherein the tracker is connectable to the coupler body in at least two different orientations.

4. The robotic surgical system of claim 1, wherein the tracker has a planar front surface and the tracking elements are visible from the planar front surface.

5. The robotic surgical system of claim 4, wherein a portion of the coupler body between the first and second side has a planar mounting surface and wherein the mounting features are located on the planar mounting surface of the coupler body.

6. The robotic surgical system of claim 1, wherein the tracker is single use and disposable.

7. The robotic surgical system of claim 1, wherein the coupler body has a generally cylindrical shape.

8. The robotic surgical system of claim 1, wherein the second mounting interface is connectable to the first mounting interface.

9. The robotic surgical system of claim 8, wherein the plurality of second mounting elements are shaped and arranged to engage the plurality of first mounting elements when connecting the second mounting interface to the first mounting interface.

10. The robotic surgical system of claim 1, wherein the plurality of first coupling elements are shaped to engage, by surface contact, the plurality of first mounting elements of the first mounting interface when connecting the first coupling interface to the first mounting interface and the plurality of second coupling elements are shaped to engage, by surface contact, the plurality of second mounting elements when connecting the second coupling interface to the second mounting interface.

11. The robotic surgical system of claim 10, wherein the plurality of first coupling elements includes a flat block and a V-shaped block and the plurality of second coupling elements includes a pair of semi-cylindrically shaped surfaces.

12. The robotic surgical system of claim 10, wherein the plurality of first coupling elements include first kinematic coupling elements and the plurality of second coupling elements include second kinematic coupling elements.

13. The robotic surgical system of claim 1, wherein the coupler and the drape are further defined as a sterile coupler and a sterile drape.

14. The robotic surgical system of claim 1, wherein the drape is connectable to the coupler.

15. The robotic surgical system of claim 1, wherein the distal link includes a first mounting flange that includes the first mounting interface and the drape is shaped to be disposed between the first mounting flange and the coupler.

16. A coupler for use with a drape to create a sterile field barrier between a cutting tool and a robotic manipulator, wherein the robotic manipulator includes a first mounting interface having a plurality of first mounting elements and the cutting tool includes a second mounting interface having a plurality of second mounting elements, the second mounting interface being connectable to the first mounting interface, the coupler comprising:

a coupler body including a first side and an opposing second side;

a first coupling interface integrated on the first side of the coupler body, the first coupling interface being directly connectable to the first mounting interface;

a second coupling interface integrated on the second side of the coupler body, the second coupling interface being directly connectable to the second mounting interface;

mounting features formed on the coupler body at a location between the first side and the second side; and a tracker supporting tracking elements and comprising attachment features configured to releasably attach coupled to the mounting features of the coupler body, wherein the tracker is configured to be detected by a localizer, wherein the first coupling interface has a plurality of first coupling elements arranged to align with and engage the first mounting elements when connecting the coupler to the robotic manipulator and the second coupling interface has a plurality of second coupling elements arranged to align with and engage the second mounting elements when connecting the coupler to the cutting tool.

17. The coupler of claim 16, wherein the second coupling interface is connectable to the second mounting interface in at least two different orientations.

18. The coupler of claim 16, wherein the tracker is connectable to the coupler body in at least two different orientations.

19. The coupler of claim 16, wherein the tracker has a planar front surface and the tracking elements are visible from the planar front surface.

20. The coupler of claim 19, wherein a portion of the coupler body between the first and second side has a planar mounting surface and wherein the mounting features are located on the planar mounting surface of the coupler body.

21. The coupler of claim 16, wherein the tracker is single use and disposable.

22. The coupler of claim 16, wherein the coupler body has a generally cylindrical shape.

23. The coupler of claim 16, wherein the plurality of first coupling elements include first kinematic coupling elements shaped and arranged to engage the first mounting elements of the first mounting interface when connecting the first coupling interface to the first mounting interface and the plurality of second coupling elements include second kinematic coupling elements shaped and arranged to engage the second mounting elements of the second mounting interface when connecting the second coupling interface to the second mounting interface.

24. The coupler of claim 23, wherein the plurality of first coupling elements includes a flat block and a V-shaped block and the plurality of second coupling elements includes a pair of semi-cylindrically shaped surfaces.

* * * * *